United States Patent
Yoshimizu et al.

(10) Patent No.: US 9,110,058 B2
(45) Date of Patent: Aug. 18, 2015

(54) POROUS SOLID PHASE FOR BINDING ASSAY, AND BINDING ASSAY METHOD USING THE SAME

(75) Inventors: Miwako Yoshimizu, Ryugasaki (JP); Mayumi Kondo, Ryugasaki (JP); Masashi Tanno, Ryugasaki (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 514 days.

(21) Appl. No.: 13/000,110

(22) PCT Filed: Jun. 30, 2009

(86) PCT No.: PCT/JP2009/003038
§ 371 (c)(1),
(2), (4) Date: Jan. 14, 2011

(87) PCT Pub. No.: WO2010/001598
PCT Pub. Date: Jan. 7, 2010

(65) Prior Publication Data
US 2011/0104709 A1 May 5, 2011

(30) Foreign Application Priority Data

Jun. 30, 2008 (JP) ................................. 2008-171367
Mar. 31, 2009 (JP) ................................. 2009-086378

(51) Int. Cl.
*G01N 33/543* (2006.01)
(52) U.S. Cl.
CPC ................................ *G01N 33/54393* (2013.01)
(58) Field of Classification Search
None
See application file for complete search history.

(56) References Cited

U.S. PATENT DOCUMENTS

| 4,990,457 | A | | 2/1991 | Tanaka et al. |
| 5,547,833 | A | * | 8/1996 | Dorval et al. ............... 435/5 |
| 5,753,497 | A | | 5/1998 | Bernstein et al. |
| 5,753,519 | A | * | 5/1998 | Durst et al. ............... 436/518 |
| 5,871,905 | A | * | 2/1999 | Thieme et al. ............... 435/5 |

(Continued)

FOREIGN PATENT DOCUMENTS

| EP | 1 167 973 A1 | 1/2002 |
| EP | 1 333 582 A2 | 8/2003 |

(Continued)

OTHER PUBLICATIONS

European Search Report issued Aug. 4, 2011, in European Patent Application No. 09773176.4.

(Continued)

*Primary Examiner* — Bao Thuy L Nguyen
*Assistant Examiner* — Gary E Hollinden
(74) *Attorney, Agent, or Firm* — Birch, Stewart, Kolasch & Birch, LLP

(57) ABSTRACT

A porous solid phase for binding assay that enables a test sample such as whole blood to be analyzed promptly, conveniently, accurately, and inexpensively without requiring a pretreatment, and a binding assay method using said porous solid phase are disclosed. At least one surfactant is incorporated into the porous solid phase for binding assay prior to addition of a test sample, the at least one surfactant being selected from the group consisting of (A) a sugar-containing surfactant that comprises a compound shown by a general formula (I), (B) a sugar-containing surfactant that comprises a sucrose fatty acid ester wherein the constituent fatty acid has 5 to 14 carbon atoms, and (C) a steroid surfactant.

13 Claims, 9 Drawing Sheets

(56) References Cited

U.S. PATENT DOCUMENTS

| | | | |
|---|---|---|---|
| 6,605,444 | B1 | 8/2003 | Klein et al. |
| 7,241,628 | B2 | 7/2007 | Schaffler et al. |
| 8,431,351 | B2 | 4/2013 | Ito |
| 8,617,366 | B2* | 12/2013 | Winarta et al. ............ 204/403.01 |
| 2002/0025541 | A1* | 2/2002 | Nelson et al. .................. 435/7.9 |
| 2002/0155623 | A1 | 10/2002 | Takahashi et al. |
| 2002/0160428 | A1 | 10/2002 | Sundrehagen |
| 2003/0044316 | A1* | 3/2003 | Hirai et al. ....................... 422/56 |
| 2003/0166295 | A1 | 9/2003 | Fukuoka et al. |
| 2004/0180444 | A1* | 9/2004 | Rannikko et al. ................ 436/14 |
| 2005/0084862 | A1* | 4/2005 | Lee et al. ........................... 435/6 |
| 2005/0130177 | A1 | 6/2005 | Bedingham et al. |
| 2005/0239214 | A1* | 10/2005 | Bohannon et al. ............. 436/514 |
| 2005/0255608 | A1* | 11/2005 | Bohannon et al. ............. 436/514 |
| 2005/0266574 | A1* | 12/2005 | Kosaka ............................ 436/86 |
| 2006/0141639 | A1* | 6/2006 | Bauer et al. ................... 436/514 |
| 2006/0172357 | A1* | 8/2006 | Yang et al. .................... 435/7.92 |
| 2007/0184506 | A1 | 8/2007 | Klepp |
| 2008/0145940 | A1* | 6/2008 | Menon ............................. 436/71 |
| 2008/0166821 | A1 | 7/2008 | Oyamada et al. |
| 2008/0279725 | A1* | 11/2008 | Nirasawa et al. .......... 422/82.13 |
| 2010/0112725 | A1* | 5/2010 | Babu et al. .................... 436/518 |
| 2010/0221747 | A1 | 9/2010 | Ito |
| 2012/0064538 | A1 | 3/2012 | Ito |

FOREIGN PATENT DOCUMENTS

| | | |
|---|---|---|
| EP | 1 739 426 A1 | 1/2007 |
| EP | 1 806 578 A1 | 7/2007 |
| EP | 1 909 103 A1 | 4/2008 |
| JP | 62-194459 A | 8/1987 |
| JP | 9-184837 A | 7/1997 |
| JP | 2000-502451 A | 2/2000 |
| JP | 2001-221797 A | 8/2001 |
| JP | 2005-77301 A | 3/2005 |
| JP | 2007-51979 A | 3/2007 |
| JP | 2007-187664 A | 7/2007 |
| JP | 2008-139297 A | 6/2008 |
| JP | 2008-203135 A | 9/2008 |
| WO | WO 95/18970 A1 | 7/1995 |
| WO | WO 96/24062 A1 | 8/1996 |
| WO | WO 2006/116917 A2 | 11/2006 |
| WO | WO 2007/069673 A1 | 6/2007 |

OTHER PUBLICATIONS

International Search Report, dated Aug. 25, 2009, issued in corresponding International Application PCT/JP2009/003038.

Machine English translation of JP 2007-051979 published Mar. 3, 2007.

European Office Action dated Apr. 23, 2014, issued in corresponding European Patent Application No. 09 773 176.4.

First Office Action issued Apr. 8, 2013 by State Intellectual Property Office of People's Repbulic of China.

International Preliminary Report on Patentability issued in International Application No. PCT/JP2009/003038 on Feb. 8, 2011, and English translation of the Written Opinion of the International Searching Authority.

\* cited by examiner

POROUS SOLID PHASE FOR BINDING ASSAY, AND BINDING ASSAY METHOD USING THE SAME

TECHNICAL FIELD

The present invention relates to an improved porous solid phase for binding assay, which prevents the problems of poor flow progression of the test sample, poor sensitivity, and disturbance of the measurement waveform that are associated with the binding assays in which porous solid phases (e.g. membranes) are used for detecting test sample components. The present invention also relates to a binding assay method that uses the said porous solid phase. More specifically, the present invention provides a porous solid phase for binding assay (binding assay porous solid phase) in which at least one surfactant has been incorporated prior to addition of a test sample, the at least one surfactant being selected from the group consisting of: (A) a sugar-containing surfactant that comprises a compound shown by the general formula (I), (B) a sugar-containing surfactant that comprises a sucrose fatty acid ester wherein the constituent fatty acid has 5 to 14 carbon atoms, and (C) a steroid surfactant, and a binding assay method that uses the said binding assay porous solid phase.

BACKGROUND ART

When a binding assay (e.g., immunochromatography) that detects a test sample component using a porous solid phase (e.g., membrane) is performed, poor flow progression of the test sample in the porous solid phase may occur due to various reasons. For example, the poor flow progression of the test sample may occur when the test sample contains a substance (e.g., blood cell) that is larger than the pores of the porous solid phase and therefore cannot easily migrate/pass through the pores of the porous solid phase, or when a component that has been solubilized in the test sample becomes insoluble during the assay and clogs the porous solid phase. In such cases, the analytes, free labeled-antibodies, and the complexes of the analytes and the labeled antibodies, as well as other substances (e.g. oxidases) that are contained in the test sample and may have similar activities as the marker substances of the detection reagents, all of which are normally expected to migrate/pass freely through the porous solid phase, may cease to migrate/pass through it and may linger in undesired locations in the porous solid phase. As a result, the expected signal intensity normally associated with a presence of the analyte may be lost, which makes the detection difficult (making the assay impossible or causing false negative results), or non-specific reactions that interfere with the detection of the signals may occur (making the assay impossible or causing false positive results), so that the reliability or reproducibility of the test may deteriorate.

Conventionally, clogging of the porous solid phase has been prevented by removing impurities (e.g., a substance (e.g., blood cell) that is larger than the pores of the porous solid phase, or a component that easily becomes insoluble) contained in the test sample, by centrifugation or filtration or via precipitation, adsorption, or the like under specific conditions, before applying the test sample to the porous solid phase. However, each of the above manipulations is time-consuming, and a loss of the test sample is unavoidable during the manipulation. Moreover, these manipulations require extra costs. If the test sample contains infectious pathogenic microorganisms, the persons who carry out the test (e.g., physicians or researchers) may be subjected to a high risk of infection.

Methods that involve addition of surfactants to incubation media (e.g., Patent Document 1) have been widely used for the purpose of preventing non-specific interferences during the binding assays. However, depending on the type of the surfactant added, a capture reagent (e.g., antibody) bound to the solid-phase carrier may be removed from the carrier, or a binding reaction between the solid-phase carrier and the antibody may be hindered in the first place, so that the specific signal may decrease considerably and the desired detection sensitivity may not be achieved. Also, when the above method is applied to a binding assay that utilizes a porous solid phase, even if the surfactant (e.g., the glycoside surfactant disclosed in Patent Document 1) does not affect the detection sensitivity per se, the absolute amount of the test sample component in the assay system may be decreased due to dilution of the test sample, so that, in effect, the desired detection sensitivity may not be ensured. Moreover, Patent Document 1 only aims at preventing non-specific interferences. In Patent Document 1, poor flow progression of the test sample is neither mentioned nor suggested, and therefore it is not recognized as a problem to be solved.

In an immunoassay where whole blood is used as a test sample, the pretreatment of the test sample with centrifugation may be omitted if a blood cell separation pad is provided between the whole blood loading area and the porous solid phase (membrane) on the binding assay strip. According to this method, the blood cell components are retained in the separation pad and prevented from flowing into the porous solid phase over a short period of time, while the plasma components are allowed to flow into the immunochromatography membrane ahead of the blood cell components; thus the assay is not affected by the presence of the blood cell components.

Even in this case, however, poorness of sample flow progression (migration or passage) may still occur due to reasons other than clogging caused by the size of the impurities. Examples of these other reasons include a high viscosity of test sample, and drying of the porous solid phase during the assay. Highly viscous test samples (e.g., a test sample that contains a large amount of solid components such as blood cells or a large amount of proteins, or a test sample which has lost water due to evaporation) inherently have poor fluidity and therefore take long time to make progression in the porous solid phase, resulting in uneven progression and a lack of assay reproducibility.

Conventionally, when a test sample that contains solid components or has high viscosity (e.g., blood (whole blood), plasma, serum, saliva, sputum, or feces) is assayed by immunochromatography, it is necessary to dilute the test sample with an appropriate diluent (incubation medium) in advance. Phosphate buffered saline (PBS) or the like is used as the diluent, and bovine serum albumin (BSA) or the like is commonly added to the diluent in order to improve the dispersibility of the test sample. However, commercially available BSA may contain impurities such as immunoglobulin which may cause non-specific reactions. The problems associated with the inclusion of a surfactant in the diluent have been mentioned above. Also mentioned above is the fact that any attempts at solving the problems by modifying the constituents of the diluent will still suffer from the most fundamental problem, namely a reduction in the amount or concentration of the analyte available for the assay, caused by the dilution.

It has been reported (Patent Document 2) that, when a porous membrane for chromatographic assay is laminated for increasing its mechanical strength and for preventing evaporation (drying) of the fluid during the chromatographic assay, the porous membrane may become less hydrophilic due to the effect of an adhesive component used in the lamination, causing poor flow progression of the test sample. Patent Document 2 solves this poor flow progression problem by improving the hydrophilicity of the membrane based on an alternative choice of adhesive component along with a treatment of the membrane with an alkylsulfonic acid surfactant prior to lamination. However, Patent Document 2 does not recognize, or present a solution to, the problem of poor flow progression associated with test samples containing solid components or having high viscosity.

As a component in an enzyme immunoassay which uses a porous membrane as a solid-phase carrier, Patent Document 3 discloses a washing solution for the enzyme immunoassay solid phase that contains an alkyl glycoside surfactant or a steroid surfactant. The washing solution disclosed in Patent Document 3 is used for the purpose of washing off the test sample-derived substances that could cause non-specific reactions, or free marker substances, which have failed to pass/migrate through the porous membrane and thus remained on the membrane, after the test sample or the marker substances (which are capable of immunologically binding the analytes in the test sample) are added to the solid-phase carrier. The washing solution disclosed in Patent Document 3 is added to the solid-phase carrier separately from the test sample, and following the immunological reaction, for the purpose of removing the substances remaining on the porous membrane. Therefore, it requires a separate preparation step and a separate addition step independent of the test sample, making the assay procedure more complicated. The method of Patent Document 3 has been conceived by assuming a situation where some substances will remain on the membrane and need to be washed off, and thus it does not contain any consideration for preventing clogging of the membrane in the first place. Therefore, poor flow progression of the test sample, which is the problem addressed in the present invention, cannot be improved by the method disclosed in Patent Document 3.

A flow-through assay, such as the one described in the examples of Patent Document 3, may include a washing step. However, when testing a number of test samples at once, such an assay may require an auxiliary means such as pressurization and suction (e.g., increasing the volume of the water-absorbing pad under the membrane) in order to obtain reproducible results within a practical time frame, making the assay system less advantageous in terms of convenience and cost.

A method involving a use of a non-ionic surfactant for washing a solid substrate (array) on which physiologically active substances are immobilized has been disclosed (Patent Document 4). Patent Document 4 discloses an alkyl glucoside surfactant as the non-ionic surfactant. However, the invention of Patent Document 4 relates to an assay in which the array (having proteins or peptides immobilized thereon) is used for detecting the protein kinase activities contained in the lysates prepared from cultured cells, and its method involves washing the array prior to the detection in order to prevent the lysate components from being non-specifically adsorbed on the surface of the array substrate. Specifically, the method involves adding the surfactant-containing washing solution onto the array and then draining it from the array. Thus, the sole objective of Patent Document 4 is prevention of non-specific reactions, and similarly to Patent Document 1 discussed above, Patent Document 4 neither mentions nor suggests the issue of poor flow progression of test samples, not recognizing this issue as a problem to be solved.

In immunochromatography, the detection of the complex of the analyte and the detection reagent may be carried out by measuring the intensities of the reflected lights and calculating the absorbance (reflection absorbance) based on the measured intensities. The reflection absorbance is calculated from the ratio of the reflected light intensities measured at the measurement line and at its adjacent areas, but in this procedure, the measurement waveform (profile) may sometimes show disturbance near the measurement line (where the complex is detected) on the upstream or downstream side (particularly on the downstream side) due to an elevated intensity of the reflected light therein. When the concentration of the analyte contained in the test sample (specimen) is low, this disturbance of the measurement waveform cannot be ignored in determining the baseline. Thus, accuracy of detection of specific signals (peaks) may be lost, and the measurement itself may be rendered impossible. Since such disturbance of measurement waveform does not appear at a fixed frequency or to a fixed extent, the reproducibility of the assay is reduced, and an appropriate correction of the measured value (i.e. evaluation of the measurement waveform) may be necessary in each measurement.

In a common immunochromatography that uses a white membrane and optical detection means, the disturbance of measurement waveform may be recognized even with the naked eye, as a phenomenon in which the corresponding area on the membrane becomes whiter, as if bleached out, than the surrounding areas.

No prior arts have addressed the problem of the disturbance of the measurement waveform, and therefore no known solution exists for this problem.

REFERENCES CITED

Patent Documents

Patent Document 1: JP-A-H06-235730
Patent Document 2: JP-A-H03-120468
Patent Document 3: JP-A-H10-332697
Patent Document 4: JP-A-2008-92905

DISCLOSURE OF THE INVENTION

Problems to be Solved by the Invention

An object of the present invention is to provide a binding assay porous solid phase that enables a test sample (e.g., whole blood) to be analyzed promptly, conveniently, accurately, and inexpensively without requiring a pretreatment (e.g., centrifugation) of the sample or an additional manipulation after the addition of the test sample, and a binding assay method using the said porous solid phase.

Means for Solving the Problems

The inventors have conducted extensive research on how to prevent the problems of poor flow progression of the test sample in the porous solid phase, poor sensitivity, poor reproducibility, and disturbance of measurement waveforms that are associated with the binding assays that detect test sample components using porous solid phases (e.g., membranes), which has let to the completion of the present invention.

Specifically, the present invention provides: a binding assay porous solid phase in which at least one surfactant has been incorporated prior to addition of a test sample, the at least one surfactant being selected from the group consisting of (A) a sugar-containing surfactant that comprises a compound shown by the general formula (I), (B) a sugar-containing surfactant that comprises a sucrose fatty acid ester wherein the constituent fatty acid has 5 to 14 carbon atoms, and (C) a steroid surfactant, and; a binding assay method using the said binding assay porous solid phase. The details are given in [1]-[24] below.

[1] A porous solid phase for binding assay in which at least one surfactant has been incorporated prior to addition of a test sample, the at least one surfactant being selected from the group consisting of:
(A) a sugar-containing surfactant that comprises a compound shown by the following general formula (I),

wherein $R^1$ represents a substituted or unsubstituted linear or branched alkyl group having 5 to 10 carbon atoms, G represents a residue derived from a reducing sugar having 5 or 6 carbon atoms, and x is a number from 1 to 3 that indicates the degree of condensation of the reducing sugar, and $R^1$ and G are linked by an ether bond via an oxygen atom or a sulfur atom,
(B) a sugar-containing surfactant that comprises a sucrose fatty acid ester wherein the constituent fatty acid has 5 to 14 carbon atoms, and
(C) a steroid surfactant.

[2] The porous solid phase for binding assay according to [1], wherein the sugar-containing surfactant (A) is n-octyl-β-D-glucoside and/or n-heptyl-β-D-thioglucoside.

[3] The porous solid phase for binding assay according to [1], wherein the sugar-containing surfactant (B) is sucrose monocaproate and/or sucrose monolaurate.

[4] The porous solid phase for binding assay according to [1], wherein the steroid surfactant (C) is sodium cholate and/or 3-[(3-cholamidopropyl)dimethylammonio]-2-hydroxypropanesulfonic acid (CHAPS).

[5] The porous solid phase for binding assay according to any one of [1] to [4], wherein the binding assay is an immunoassay.

[6] The porous solid phase for binding assay according to any one of [1] to [5], wherein the binding assay is a lateral-flow format, dipstick format, or flow-through format membrane assay.

[7] The porous solid phase for binding assay according to any one of [1] to [6], wherein a capture reagent is immobilized on the porous solid phase.

[8] The porous solid phase for binding assay according to [7], wherein the capture reagent is an antibody, a specific capture substance, or an antigen.

[9] A binding assay strip comprising the porous solid phase according to any one of [1] to [8].

[10] The binding assay strip according to [9], further comprising a conjugate release pad that comprises a detection reagent.

[11] The binding assay strip according to [10], wherein the detection reagent is a labeled antibody, a labeled specific capture substance, or a labeled antigen.

[12] The binding assay strip according to [11], wherein the label comprises two types of colloidal gold that differ in particle diameter.

[13] The binding assay strip according to any one of [10] to [12], wherein the conjugate release pad comprises an amino acid.

[14] The binding assay strip according to [9], further comprising a sample pad and/or a blood cell separation pad.

[15] The binding assay strip according to [14], wherein the sample pad comprises an anticoagulant.

[16] A binding assay strip for a lateral-flow format binding assay, comprising:
(1) a sample pad;
(2) a conjugate release pad that comprises a detection reagent and is placed beneath the sample pad in contact with the sample pad;
(3) a blood cell separation pad that is placed between the conjugate release pad and a porous solid phase (4) below; and
(4) the porous solid phase on which a capture reagent is immobilized,
wherein the porous solid phase is the porous solid phase for binding assay according to any one of [1] to [8].

[17] A device comprising the binding assay strip according to any one of [9] to [16].

[18] A binding assay method implemented by the use of the porous solid phase according to any one of [1] to [8].

[19] A binding assay method implemented by the use of the binding assay strip according to any one of [9] to [16].

[20] A binding assay method that tests a presence of a complex of a detection reagent and an analyte that forms when a test sample migrates and/or passes through the porous solid phase according to [1], the analyte being originating from the test sample and captured by a capture reagent immobilized on the said porous solid phase.

[21] The binding assay method according to any one of [18] to [20], wherein the test sample is whole blood.

[22] A method of preventing poor flow progression of a test sample in a lateral-flow or dipstick format binding assay, comprising a use of a porous solid phase for binding assay in which at least one surfactant has been incorporated prior to addition of the test sample, the at least one surfactant being selected from the group consisting of:
(A) a sugar-containing surfactant that comprises a compound shown by the following general formula (I),

wherein $R^1$ represents a substituted or unsubstituted linear or branched alkyl group having 5 to 10 carbon atoms, G represents a residue derived from a reducing sugar having 5 or 6 carbon atoms, and x is a number from 1 to 3 that indicates the degree of condensation of the reducing sugar, and $R^1$ and G are linked by an ether bond via an oxygen atom or a sulfur atom,
(B) a sugar-containing surfactant that comprises a sucrose fatty acid ester wherein the constituent fatty acid has 5 to 14 carbon atoms, and
(C) a steroid surfactant.

[23] The method according to [22], wherein the test sample has an Ht value of 50% or higher.

[24] A method of preventing disturbance in a measurement waveform of a test sample in a lateral-flow or dipstick format binding assay, comprising a use of a porous solid phase for binding assay in which at least one surfactant has been incorporated prior to addition of the test sample, the at least one surfactant being selected from the group consisting of:
(A) a sugar-containing surfactant that comprises a compound shown by the following general formula (I),

wherein $R^1$ represents a substituted or unsubstituted linear or branched alkyl group having 5 to 10 carbon atoms, G represents a residue derived from a reducing sugar having 5 or 6 carbon atoms, and x is a number from 1 to 3 that indicates the degree of condensation of the reducing sugar, and $R^1$ and G are linked by an ether bond via an oxygen atom or a sulfur atom,
(B) a sugar-containing surfactant that comprises a sucrose fatty acid ester wherein the constituent fatty acid has 5 to 14 carbon atoms, and
(C) a steroid surfactant.

Effects of the Invention

The present invention provides: a novel binding assay porous solid phase that is used for a binding assay in which the detection of a test sample component is carried out by using a porous solid phase, comprising at least one surfactant prior to addition of the test sample, the at least one surfactant being selected from the group consisting of (A) a sugar-containing surfactant that comprises a compound shown by the general formula (I), (B) a sugar-containing surfactant that comprises a sucrose fatty acid ester wherein the constituent fatty acid has 5 to 14 carbon atoms, and (C) a steroid surfactant, and; a novel binding assay method using the said porous solid phase. According to the present invention, it is possible to perform a binding assay with excellent reproducibility, in which poor flow progression of the test sample in the porous solid phase is prevented, and in particular, false negatives and false positives that would be otherwise seen with a test sample that contains a solid component or has high viscosity are prevented. Since neither a pretreatment of the test sample (including preparation of a diluent or a washing solution) nor a washing step after the addition of the test sample is necessary, the operation is easy and convenient. Moreover, the present invention enables a superb assay performance characterized with high sensitivity and lack of disturbance in the measurement waveform.

BEST MODE FOR CARRYING OUT THE INVENTION

Figure 1:
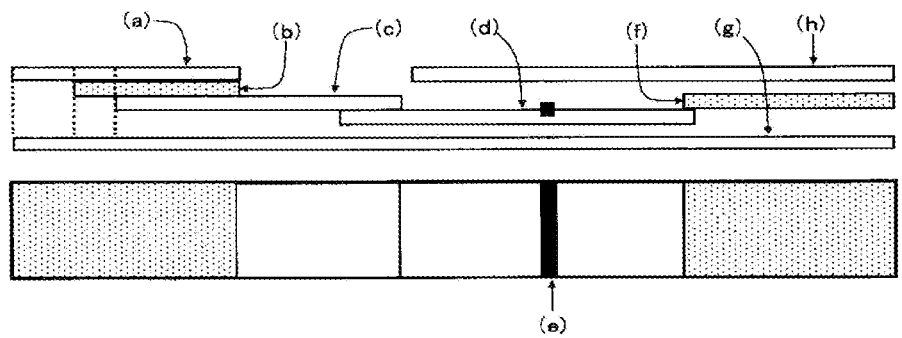
FIG. 1 shows a schematic configuration diagram of a binding assay strip (test strip).

The term "test sample" used herein refers to blood (whole blood), serum, plasma, lymph, urine, feces, ascites, pleural effusion, tissues/cells, and the like. The term "test sample" used herein includes a test sample component separated/fractionated from whole blood or the like by centrifugation, filtration, purification, or the like, a test sample component extracted with an organic solvent or the like, a test sample component solubilized with a surfactant or the like, a test sample component diluted with a buffer or the like, a test sample component modified/altered by a chemical reaction or the like, and so on, that may be subjected to the assay using the binding assay porous solid phase according to the present invention. A test sample of the present invention is liquid (fluid) at the time it is added to, and makes progression in, the binding assay porous solid phase according to the present invention. Test samples of the present invention may also include such things as plant, river water, and soil. The term "progression" used herein comprises both "migration" which refers to the flow of liquid in the horizontal direction as the porous solid phase is placed with its largest surface facing upward (i.e. the flow in the porous solid phase lengthwise) and "passage" which refers to the flow of liquid in the vertical direction as the porous solid phase is placed with its largest surface facing upward (i.e. the flow of liquid across the thickness of the porous solid phase).

Preferred embodiments of the present invention are described below, in which whole blood is mainly used as an example of test sample.

The term "test sample component" used herein refers to a component contained in the test sample. Specific examples of the test sample components include: coagulation or fibrinolysis markers such as fibrin degradation products (e.g., D-dimer), soluble fibrin, TAT (thrombin-antithrombin complex), and PIC (plasmin-plasmin inhibitor complex); cardiovascular-related markers such as oxidized LDL and BNP (brain natriuretic peptide); metabolism-related markers such as adiponectin, tumor markers such as CEA (carcinoembryonic antigen), AFP (α-fetoprotein), CA19-9, CA125, and PSA (prostate-specific antigen); inflammation-related markers such as CRP (C-reactive protein), IgA, IgG, and IgM; infectious disease-related markers such as influenza, HIV (human immunodeficiency virus), HBV (hepatitis B virus), HCV (hepatitis C virus), toxoplasma, chlamydia, and syphilis; allergen-specific IgE (immunoglobulin E), hormones, drugs, nucleic acid chains and fragments thereof that involve single nucleotide polymorphisms (SNPs), and the complementary strands of the said nucleic acid chains. The term "test sample component" may herein also be referred to as "analyte".

The present invention's advantageous effect of preventing the poor flow progression in the porous solid phase of the test samples that contain solid components or have high viscosity may be most beneficial for, for example, whole blood sample that contains a high proportion of blood cells and a less-than-normal amount of plasma and has a high hematocrit (Ht) value (referred to as "high Ht value sample"), or a test sample that lacks fluidity due to a high protein content or other reasons (referred to as "high viscosity test sample"). These test samples have low water (liquid) contents. Examples of the high Ht value samples include samples having a Ht value of 50% or higher which exceeds the standard range. The high Ht value may be due to an increase of red blood cells caused by some disease, or an abnormal decrease of the plasma volume per unit amount of whole blood caused by dehydration, for example. The test samples that have, for one reason or another, suffered evaporation of water and been dried/concentrated after they were collected or after the binding assay was initiated may also benefit from the present invention.

The term "capture reagent" used herein refers to a reagent that specifically binds to and forms a complex with the test sample component, and may include an antibody to an antigen, a "specific capture substance", and an antigen to an antibody. The term "specific capture substance" includes a receptor for a ligand, a complementary strand or an aptamer for a nucleic acid chain, a lectin for a specific sugar-containing substance, and the like. A person having ordinary skill in the art would readily appreciate that, depending on the choice of analyte to be tested, the design of the assay system, etc., a test sample component (e.g. antigen to antibody) of the present invention recognized as such in one situation may become a capture reagent of the present invention in another situation. A person having ordinary skill in the art would also readily appreciate that the capture reagent may be of any type as long as it can form a complex with the test sample component, and may be a whole substance or a functional fragment thereof. For example, if the capture reagent is an antibody, it may be a polyclonal antibody, a monoclonal antibody, a functional fragment thereof (e.g., Fab, Fab', F(ab')$_2$, and Fv), and so on.

The term "detection reagent" used herein is synonymous with the term "conjugate", and refers to a capture reagent that is labeled with a detection marker, or something that has the same properties as, or is equivalent in the binding assay to, the labeled analyte. Specific examples of the detection reagents include a labeled antibody, a labeled specific capture substance, a labeled antigen, and the like. Examples of the known markers include visualizable microparticles such as metal colloid particles (e.g., colloidal gold) and colored latex particles, enzymes such as horseradish peroxidase, alkaline phosphatase, and β-D-galactosidase, radioisotopes such as iodine-125 ($^{125}$I), luminescent substances such as acridinium compounds and luminol, fluorescent substances such as fluorescein isothiocyanate and a europium (III) chelate, and the like. The antibody or the like may be labeled by any known labeling method (i.e., a method of introducing and binding a marker substance) without limitation.

The term "sample pad" used herein refers to a part that accepts the test sample that may contain the test sample component (analyte), and includes any material or shape that can, in the form of a pad, absorb a liquid test sample and allow the liquid and the test sample component to pass through. Specific examples of materials suitable for the sample pad include, but are not limited to, glass fibers, acrylic fibers, hydrophilic polyethylene materials, dry papers, pulp, fabrics, and the like. It is preferable to use a glass fiber pad (manufactured by Lydall) as sample pad. The sample pad may function as a sample pad per se, or may additionally be given the functional role of a conjugate release pad or a blood cell separation pad which usually accepts the test sample from the sample pad.

The sample pad may comprise a blocking reagent or the like that is commonly used in binding assays in order to prevent or suppress non-specific reactions (adsorption) inside the binding assay porous solid phase. Examples of such a reagent include HeteroBlock ("500-11-001" manufactured by Omega Biologicals, Inc.) and the like. Further, the sample pad may comprise one or more anticoagulants, for example, in order to prevent blood coagulation and suppress non-specific reactions that would occur due to blood coagulation during the assay (in particular, before the analyte reaches the porous solid phase). As anticoagulant, heparin, citric acid, sodium fluoride (NaF), or a chelating agent (or salt or hydrate thereof) may be used, as long as the effects of the present invention are not impaired by it. Examples of the chelating agent include EDTA, CyDTA, DTPA, and the like.

The term "conjugate release pad" used herein refers to a part that contains a detection reagent that specifically reacts with the test sample component, and allows the detection reagent and the test sample component to form a complex through the specific reaction when the test sample passes through the conjugate release pad. The conjugate release pad may be placed adjacent to the porous solid phase by itself. Alternatively, the conjugate release pad may be placed in contact with the sample pad on one side and also with a blood cell separation pad (described below) on the other side, so that it accepts the test sample that has passed through the sample pad by a capillary flow and then transports the test sample to the blood cell separation pad also by a capillary flow. A person having ordinary skill in the art would readily appreciate that the choice of one or more of the sample pad, the conjugate release pad, and the blood cell separation pad, and how the chosen parts are placed relative to the porous solid phase for binding assay, may be changed as appropriate depending on the intended purpose of the strip design and the like.

Examples of a material suitable for conjugate release pad include, but are not limited to, paper, a cellulose mixture, nitrocellulose, polyester, an acrylonitrile copolymer, glass fibers, and nonwoven fibers (e.g., rayon). It is preferable to use a glass fiber pad ("No. 8964" manufactured by Pall Corporation) as conjugate release pad.

The conjugate release pad may comprise a "control reagent" to ensure the reliability of the assay, such as a marker-labeled antibody that does not react with the test sample component, and a highly antigenic protein (e.g., keyhole limpet hemocyanin (KLH)) that is labeled with a marker. The control reagent may be any component (substance) that is not expected to be present in the test sample and makes appropriate combination with a control capture reagent (described below). The conjugate release pad may further comprise one or more of stabilizer, solubilizer and the like, so that the detection reagent (and optionally the control reagent) is maintained in a stable state and becomes dissolved and fluidized promptly and effectively upon contact with the test sample, to facilitate the specific reaction between the detection reagent and the analyte that may be contained in the test sample. Examples of the stabilizer and the solubilizer include bovine serum albumin (BSA), sucrose, casein, amino acids, and the like. The amino acid is preferably glycine or serine.

The term "blood cell separation pad" used herein refers to a part that is placed adjacent to the said conjugate release pad so that the blood cell separation pad receives the test sample that has passed through the conjugate release pad by a capillary flow, and then transports the test sample to the porous solid phase, which is placed in contact with the other side of the blood cell separation pad, by a capillary flow.

The blood cell separation pad is formed of a hydrophilic and absorptive material that has an inherent ability of filtering out part of the cellular components contained in the test sample, and, if the test sample is whole blood, that may separate part of the cellular components contained therein from the plasma or the serum. Even if the test sample does not contain cellular components, it may contain solid components that are larger than the pores of the blood cell separation pad, which may be separated in the same manner as the cellular components. Therefore, a person having ordinary skill in the art would readily appreciate that the blood cell separation pad may be used to separate not only blood cells, but also solid components in general contained in the test sample.

Examples of a material suitable for the blood cell separation pad include, but are not limited to, water-absorbing or non-water-absorbing fibrous or non-fibrous matrix such as a hydrophilic inorganic powder (e.g., silica gel, alumina, and diatomaceous earth); a sponge material; a clayey material; cloth; a hydrophilic natural polymer material such as a cellulose material (especially cellulose porous beads) and fiber-containing paper (especially filter paper or chromatography paper); and a synthetic or modified natural polymer such as cellulose acetate, polyvinyl chloride, polyacrylamide, polyacrylate, polyurethane, crosslinked dextran, agarose, and other crosslinked or non-crosslinked water-insoluble hydrophilic polymers. Further examples of a material suitable for the blood cell separation pad include, but are not limited to, a fibrous or non-fibrous matrix such as a glass fiber matrix; and a synthetic polymer such as polypropylene, polyethylene, nylon, polyvinylidene fluoride, and polysulfone. A hard porous plastic also may be useful as a material for the blood cell separation pad as long as it can separate blood corpuscle components contained in whole blood and has a sufficient porosity to allow plasma or serum to pass through and come in contact with the porous solid phase. It is preferable to use a polysulfone pad ("BTS-SP300" manufactured by Pall Corporation) as blood cell separation pad.

The term "absorber" used herein refers to a liquid-absorbing part that absorbs the test sample that has migrated/passed through the capture reagent-carrying area of the binding assay porous solid phase to control the flow progression of the test sample. In a lateral-flow or a dipstick format, the absorber may be provided on the downstream end of the strip, and in a flow-through format, the absorber may be provided beneath the membrane on which the capture reagent is immobilized, for example. Examples of the absorber include, but are not limited to, filter paper. It is preferable to use the 740-E filter paper manufactured by Whatman.

The term "porous solid phase" used herein refers to a porous membrane that is commonly used for a binding assay. The flow progression of the test sample takes place in the porous solid phase and the detection of the test sample component is ultimately carried out therein. The material for the porous solid phase is not limited, and for example, the porous solid phase may be produced from polyethylene, polyethylene terephthalate, nylon, glass, a polysaccharide (e.g., cellulose or cellulose derivative), a ceramic, or the like. Specific examples include glass fiber filter paper and cellulose filter paper available from Millipore, Toyo Roshi, and Whatman.

The capture reagent is immobilized on the porous solid phase. The capture reagent may be immobilized on the porous solid phase by any means, as long as the capture reagent becomes immobilized on the porous solid phase directly or indirectly via physical adsorption, a chemical bond, or the like. For example, an antibody or an antigen may be adsorbed and immobilized on a membrane by applying or "spotting" a solution containing the antibody or the antigen onto the membrane, and then drying the membrane. The "control capture reagent" mentioned above in connection with the conjugate release pad also may be immobilized on the porous solid phase by a similar means. The control capture reagent is a reagent for ensuring the reliability of the assay. For example, if the labeled antibody is derived from a mouse, an anti-mouse antibody (the type of the anti-mouse specificity may be chosen as appropriate) for example may be a control capture reagent. If the conjugate release pad comprises a control reagent such as labeled KLH, an anti-KLH antibody or the like may be used as a control capture reagent. The position on the porous solid phase at which the control capture reagent is immobilized may be appropriately chosen depending on the design of the assay system. For example, when a lateral-flow or dipstick format and a labeled mouse-derived antibody are used, and an anti-mouse antibody is used as a control capture reagent, the anti-mouse antibody is normally immobilized on the downstream side of the capture reagent for the test sample component. When a flow-through format is used, the anti-mouse antibody is normally immobilized at an appropriate distance (or an appropriate interval if a plurality of test sample components are being detected) from the immobilization position of the capture reagent for the test sample component. In summary, the optimal positions for immobilizing the control capture reagents may be chosen by taking account of the design of the assay system and the combination of the control reagent and the control capture reagent.

The term "strip" used herein refers to a product in which the binding assay porous solid phase is fitted with at least one of the sample pad, the conjugate release pad, the blood cell separation pad, and the absorber as appropriate. Assuming that the assay involves no dilution of the test sample and no extra steps other than the addition of the test sample, the strip may comprise at least a binding assay porous solid phase fitted with a conjugate release pad. The strip is usually formed on a solid phase support such as an adhesive plastic sheet. The solid phase support, as well as the adhesive component, should be made of a material that does not hinder the capillary flow of the test sample. The porous solid phase may be laminated for the purpose of increasing its mechanical strength and preventing evaporation (drying) of water during the assay (see Patent Document 2). When a polyester film or the like is layered on the upper side of the porous solid phase so that the porous solid phase is covered in the lamination, advantageous effects for the flow progression of the test sample, such as an improved speed of the flow progression, may be observed. The strip may be installed in or mounted on a container (housing) that is appropriate with respect to the size of the strip, the manner and the position of the addition of the test sample, the immobilization position of the capture reagent, the signal detection method, and the like. Such a product is referred to as a "device".

One of the surfactants that may be used in the present invention is (A) a sugar-containing surfactant that comprises a compound shown by the following general formula (I):

$$R^1\text{-}(G)_x \qquad (I)$$

wherein $R^1$ represents a substituted or unsubstituted linear or branched alkyl group having 5 to 10 carbon atoms, G represents a residue derived from a reducing sugar having 5 or 6 carbon atoms, and x is a number from 1 to 3 that indicates the degree of condensation of the reducing sugar, and $R^1$ and G are linked by an ether bond via an oxygen atom or a sulfur atom.

Examples of the linear or branched alkyl group having 5 to 10 carbon atoms that may be used in the present invention include, but are not limited to, pentyl group, 3-methylbutyl group, hexyl group, methylpentyl group, heptyl group, 4-methylhexyl group, 5-methylhexyl group, 4-ethylpentyl group, octyl group, 6-methylheptyl group, 5-methylheptyl group, 5,5-dimethylhexyl group, nonyl group, decyl group, and the like. The alkyl group may be substituted with any substituent as long as the effects of the present invention are not impaired by the substitution. Examples of the substituent include a halogen atom (e.g., chlorine atom, fluorine atom, and iodine atom), a hydroxyl group, and the like. A preferable $R^1$ is a linear alkyl group having 7 or 8 carbon atoms (n-heptyl group or n-octyl group).

Examples of the reducing sugar having 5 or 6 carbon atoms include glucose, galactose, and fructose. The reducing sugar may be of the α-form or the β-form, but the β-form is preferred. The reducing sugar may form a condensate with an identical or a different reducing sugar. Specific examples of the condensate include maltose (condensate of two glucose molecules), sucrose (condensate of one glucose molecule and one fructose molecule), and the like. x is a number from 1 to 3 that indicates the degree of condensation of the reducing sugar. It should be noted that x is an average value, which may be determined by the proton NMR. x is preferably from 1 to 2.

$R^1$ and G are linked by an ether bond via an oxygen atom or a sulfur atom to form a glycosidic bond or a thioglycosidic bond. A specific example of such a structure is $R^1$ and a glucose that are linked by an ether bond via an oxygen atom or a sulfur atom attached to the position 5 carbon of the glucose.

Specific examples of the compound shown by the general formula (I) include: alkyl glucoside derivatives such as n-heptyl-β-D-glucoside (n-heptyl-β-D-glucopyranoside), n-octyl-β-D-glucoside (n-octyl-β-D-glucopyranoside), n-nonyl-β-D-maltopyranoside, n-decyl-β-D-glucopyranoside, and n-decyl-β-D-maltopyranoside; alkyl thioglucoside derivatives such as n-heptyl-β-D-thioglucoside (n-heptyl-β-D-thioglucopyranoside), n-octyl-β-D-thioglucoside (n-octyl-β-D-thioglucopyranoside), n-nonyl-β-D-thiomaltopyranoside, octyl-β-D-thiogalactopiranoside, and n-dodecyl-β-D-maltoside; and the like. Among these, n-octyl-β-D-glucoside or n-heptyl-β-D-thioglucoside is especially preferable for preventing the poor flow progression of the test sample and for improving the sensitivity of the assay. For preventing the disturbance of the measurement waveform, n-octyl-β-D-glucoside, n-heptyl-β-D-thioglucoside, or n-dodecyl-β-D-maltoside is preferable.

Another surfactant that may be used in the present invention is (B) a sugar-containing surfactant that comprises a sucrose fatty acid ester wherein the constituent fatty acid has 5 to 14 carbon atoms.

Examples of the fatty acid having 5 to 14 carbon atoms include pentanoic acid (valeric acid), hexanoic acid (caproic acid), heptanoic acid (enanthic acid), octanoic acid (caprylic acid), nonanoic acid (pelargonic acid), decanoic acid (capric acid), dodecanoic acid (lauric acid), and tetradecanoic acid (myristic acid). Among these, a fatty acid having 6 or 12 carbon atoms (i.e., hexanoic acid (caproic acid) or dodecanoic acid (lauric acid)) is preferable.

The number of fatty acid molecules attached to one sucrose molecule via an ester bond may be, for example, 1 to 3. It is preferable to use a sucrose fatty acid ester in which one fatty acid molecule is attached to one sucrose molecule via an ester bond. Specific examples of such a compound include sucrose monocaproate and sucrose monolaurate.

The term "sugar-containing", in the context of "sugar-containing surfactant" as used herein, means that the surfactant selected from the group consisting of (A) a compound shown by the general formula (I) and (B) a sucrose fatty acid ester wherein the constituent fatty acid has 5 to 14 carbon atoms contains a sugar moiety or a sugar-derived moiety within its structure.

Still another surfactant that may be used in the present invention is (C) a steroid surfactant.

The term "steroid surfactant" used herein refers to an ionic or nonionic surfactant in which the hydrophobic group has a steroid skeleton. Specific examples of the steroid surfactant include cholates, deoxycholates, dehydrocholates, taurocholates, glycocholates, 3-[(3-cholamidopropyl)dimethylammonio]propanesulfonic acid, 3-[(3-cholamidopropyl)dimethylammonio]-2-hydroxypropanesulfonic acid (CHAPS), N,N-bis(3-D-gluconamidopropyl)cholamide, steroid saponin (e.g., digitonin), and the like. Among these, sodium cholate, CHAPS, and the like are preferable for preventing the poor flow progression of the test sample and for improving the sensitivity of the assay. For preventing the disturbance of the measurement waveform, sodium cholate, CHAPS, or digitonin is preferable.

The surfactants mentioned above may be used either individually or in combination. These surfactants are normally used at a concentration of 0.001 to 2.0% (w/v). A person having ordinary skill in the art would be able to determine experimentally the optimal concentration of the surfactant, taking into consideration the presence of other components/ elements besides the surfactant in the binding assay to be performed, the material of the membrane, and the like, to maximize the effects of the present invention. For example, the concentration of the surfactant is preferably in the range of 0.001 to 0.5%, more preferably 0.01 to 0.5%, and still more preferably 0.01 to 0.1%.

The surfactant of the present invention is used in the form of a solution. The surfactant may be incorporated into the porous solid phase prior to the addition of the test sample by immersing the porous solid phase in a solution of the surfactant and then drying the porous solid phase, for example.

In the method according to the present invention where the surfactant is incorporated into the porous solid phase, the test sample need not be pretreated, and a decrease in detection sensitivity due to dilution of the test sample is precluded. Moreover, if a conjugate release pad is provided, the extra step of adding the detection reagent after the addition of the test sample will be unnecessary. Therefore, a binding assay can be performed easily. The pretreatment of the test sample, which has been performed in the conventional methods, would make the assay results variable depending on the timing of the addition of the washing solution or other factors. However, the use of the porous solid phase of the present invention, comprising the surfactant in advance, not only eliminates the trouble of performing a pretreatment, but also eliminates the need of mastery (in terms of adjusting the timing of the washing solution etc.) on the part of the user, thereby improving the accuracy of the assay. The timing of the addition of the washing solution needs to be further adjusted depending on the lot-to-lot variation of the strips, but this issue is less problematic in the present invention as discussed above.

In order to maximize the effects of the present invention and to provide the most practical embodiment, it is important to immobilize the surfactant onto the porous solid phase and turn it into a dry state before use. The surfactant of the present invention needs to be immobilized at least in the test sample migration area of the porous solid phase, in the case of a lateral-flow or dipstick format. The test sample migration area of the porous solid phase starts at the section to which the test sample is introduced (either directly or through a conjugate release pad or the like), encompasses the migration path of the test sample, and ends at the section where the capture reagent is immobilized. However, it is preferable that the immobilization of the surfactant extends to the end of the porous solid phase. Also, it is important to immobilize the surfactant uniformly over the migration area of the test sample so that the test sample could migrate evenly. As described above, the porous solid phase for binding assay according to the present invention enables orderly progression (migration/passage) of a test sample, even of a high viscosity, and hence an assay with excellent reproducibility, in which the detection sensitivity is not compromised. It should be noted that the concentrations of the surfactant mentioned above are primarily intended for the method of incorporating the surfactant into the porous solid phase by immersion, mentioned above. Therefore, if a different method is employed for incorporating the surfactant into the porous solid phase, for example spraying of the surfactant onto the porous solid phase or modification/processing of the porous solid phase material itself, an appropriate concentration of the surfactant may be determined for that method, where the results obtained in the immersion method serve as reference points.

The expression "immobilize the surfactant onto the porous solid phase and turn it into a dry state before use" means a state where the surfactant is incorporated into the porous solid phase and cannot easily come off or be removed from the porous solid phase; it does not necessarily require physical adsorption or chemical bonding. Therefore, the immobilization, as the word is intended in this context, may be achieved by immersing the porous solid phase into the surfactant solution and then drying the porous solid phase. In short, it will be sufficient if the porous solid phase somehow holds the surfactant in a dry state prior to the assay.

The surfactant solution of the present invention described above may, in addition to the surfactant, further comprise a buffer that is commonly used in binding assays as a component in the blocking solution, washing solution or diluent, such as phosphate buffer, Tris buffer, and Good's buffer. The pH of the buffered solution is not limited, but is preferably in the range of 5 to 9. Furthermore, additional components that are commonly added to the buffers, such as a salt (e.g., sodium chloride) and a preservative, may be added to the surfactant solution.

Moreover, the surfactant solution of the present invention described above may, in addition to the surfactant of the present invention, further comprise an additional surfactant (e.g., polyoxyethylene nonionic surfactant such as polyoxy sorbitan monolaurate or polyoxyethylene mono-p-isooctylphenyl ether) that is commonly used in binding assays and that does interfere with the assay system, at a concentration commonly used in this technical field.

A binding assay method that utilizes the binding assay porous solid phase according to the present invention is described below by taking an immunoassay as an example. A test sample is applied to a binding assay strip that comprises a sample pad that accepts the test sample, a conjugate release pad comprising a labeled antibody (as a detection reagent), a blood cell separation pad for separating cellular components, and the porous solid phase of the present invention comprising the surfactant, on which an antibody (as a capture reagent) is immobilized. When the test sample passes through the conjugate release pad, the labeled antibody reacts with the test sample component (analyte) to form a specific complex. The complex makes progression (migration/passage) through the membrane by the capillary action, and the signal derived from the marker within the specific complex that has been captured by the antibody immobilized on the membrane is measured. In the binding assay method according to the present invention, since the surfactant is dried and immobilized beforehand on the test sample migration area of the porous solid phase, the test sample shows excellent fluidity and can migrate evenly through the porous solid phase, even when the test sample contains a solid component or is highly viscous. Moreover, the frequency of the phenomenon in which an area around the line containing the capture reagent becomes white (on the upstream or downstream side) can be reduced in the binding assay according to the present invention.

Specific examples of such immunoassays include a "flow-through format" immunoassay, a "dipstick format" immunoassay, and a "lateral-flow format" immunoassay.

In the "lateral-flow format", a liquid test sample is added dropwise to the device and allowed to progress (migrate) in the horizontal direction through the porous solid phase to which a capture reagent, which can specifically bind the test sample component (analyte), has been applied. The detection reagent that specifically binds the analyte, the analyte itself, and the capture reagent immobilized on the porous solid phase together form a ternary complex on the porous solid phase, and the marker comprised in the detection reagent is then detected or quantified. The "flow-through format" has the same assay principle as the lateral-flow format, but differs from the lateral-flow format in that a liquid test sample progresses (passes) in the vertical direction through the porous solid phase.

The "dipstick format" differs from the above two formats in that a part of the strip is dipped into a predetermined amount of a liquid test sample. Here, the progression (migration) of the test sample is achieved as the test sample ascends the porous solid phase.

The beneficial effect of preventing poor flow progression of the test sample, achieved in the porous solid phase of the present invention, will be greater with the progression distance traveled by the test sample being longer. In other words, a binding assay with excellent reproducibility can be performed when the present invention is used in combination with the "lateral-flow format" or "dipstick format" in which the test sample migrates along the longest side of the porous solid phase. Since the porous solid phase according to the present invention comprising the surfactant suppresses poor flow progression of the test sample, it is useful for a binding assay that does not include a washing step, and it is especially suitable for a lateral-flow or dipstick format binding assay.

The porous solid phase of the present invention comprising the surfactant, the conjugate release pad, and the like may be produced by modifying/altering the methods described in the following examples as appropriate. The reactions involving the test sample and the marker may be carried out in any order during the assay, as long as the porous solid phase for binding assay according to the present invention can be utilized. A signal from the marker may be measured according to commonly known methods. For example, when colloidal gold is used as the marker, the absorbance or the intensity of reflected light may be measured. When a radioisotope is used as the marker, the radiation dose may be counted by using a counter.

EXAMPLES

The present invention is further described below by way of examples. However, the present invention is not limited to the following examples.

Comparative Example 1

Production of an Immunochromatographic Device Using a Conventional Binding Assay Porous Solid Phase (1) Production of Colloidal Gold-Labeled Anti-D Dimer Antibody (Anti-DD Antibody Conjugate)

10 ml of 2 mmol/l borate buffer solution (pH 8.0) containing 92.4 µg/ml of an anti-D dimer monoclonal antibody (anti-DD antibody) was added to 200 ml of potassium carbonate buffer solution (pH 8.0) containing colloidal gold (1 OD/ml) (particle diameter: 40 nm). The mixture was stirred at room temperature for 10 minutes. After the addition of 20 ml of a 10% bovine serum albumin (BSA) aqueous solution to the colloidal gold-anti-DD antibody mixture, the mixture was stirred further for 5 minutes, and centrifuged (10,000 rpm) at 10° C. for 45 minutes to obtain a sediment (conjugate). The conjugate was diluted with (suspended in) a Conjugate Dilution Buffer (manufactured by Scripps) to 17 OD/ml. The absorbance was measured at 524 nm (i.e., the maximum absorption wavelength of the colloidal gold).

(2) Production of a Conjugate Release Pad

The conjugate prepared in (1) was mixed with a 1.33% casein and 4% sucrose solution (pH 7.5) to prepare a conjugate solution (4 OD/ml). A glass fiber pad (width: 13.0 mm, length: 254 mm, thickness: 0.56 mm) ("No. 8964" manufactured by Pall Corporation) was impregnated with 1.2 volumes (relative to the volume of the pad) of the conjugate solution. The pad was dried at 70° C. for 30 minutes in a dry oven to obtain a conjugate release pad.

(3) Production of a Membrane on which Anti-DD Antibody is Immobilized (Porous Solid Phase for Binding Assay)

A 'line' of 10 mmol/l phosphate buffer solution (pH 7.2) containing 1 mg/ml of anti-DD antibody and 2.5% sucrose was drawn (1 µl/cm) on a nitrocellulose membrane (short side: 25 mm, long side: 254 mm, thickness: 0.235 mm) ("HF240" manufactured by Millipore) at a position which was 11 mm from the edge of a long side, along the long side of the membrane, by using an immunochromatography dispenser "XYZ3050" (manufactured by BIODOT). The membrane was dried at 70° C. for 45 minutes in a dry oven to obtain a membrane on which anti-DD antibody is immobilized.

(4) Production of a Sample Pad

A glass fiber pad (short side: 16 mm, long side: 254 mm, thickness: 0.55 mm) (manufactured by Lydall) was impregnated with 1.15 volumes (relative to the volume of the pad) of the sample pad impregnation solution (20 mmol/l Tris-HCl buffer (pH 7.2) containing 25 mmol/l of NaCl, 0.5% sucrose, and 0.25 mg/ml of HETERO BLOCK ("500-11-001" manufactured by Omega Biologicals)). The pad was dried at 70° C. for 45 minutes in a dry oven to obtain a sample pad.

(5) Production of a Binding Assay Strip (Test Strip)

The above membrane on which anti-DD antibody had been immobilized (d) was bonded to an adhesive plastic sheet (g). A blood cell separation pad (c) ("BTS-SP300" manufactured by Pall Corporation) was placed at the end of the membrane opposite to the side where the anti-DD antibody (e) had been applied. An absorber (f) ("740-E" manufactured by Whatman) was placed at the other end of the membrane, namely the same side where the anti-DD antibody had been applied. A conjugate release pad (b) produced in (2) was placed to overlap the blood cell separation pad, and the sample pad (a) produced in (4) was placed to overlap the conjugate release pad. Finally, a polyester film (h) was laminated on the top to cover the porous solid phase and the absorber. The resulting structure in which these parts were layered on each other was cut to a width of 6 mm to obtain a test strip. The test strip had a width of 6 mm and a length of 70 mm. The test strip was installed in/mounted on a plastic housing (not shown in FIG. 1) which was designed specifically for this purpose and had a sample addition window and a detection window, to obtain an immunochromatographic device. FIG. 1 is a schematic configuration diagram of the test strip.

Example 1

Production of an Immunochromatographic Device Using the Test Strip According to the Present Invention (1) Production of a Membrane of the Present Invention on which Anti-DD Antibody is Immobilized (Porous Solid Phase for Binding Assay)

A nitrocellulose membrane ("HF240" manufactured by Millipore) was immersed in a 10 mmol/l phosphate buffer (pH 7.2) containing a surfactant of the present invention shown in Table 1 at a concentration of 0.05% (w/v), and shaken at room temperature for 30 minutes. After excess liquid was removed, the membrane was dried at 37° C. for 1 hour in a dry oven. The resultant membrane containing the surfactant was then processed in the same manner as in step (3) of Comparative Example 1 to obtain a membrane of the present invention on which anti-DD antibody was immobilized.

(2) Production of an Immunochromatographic Device of the Present Invention

A test device of the present invention was produced in the same manner as in step (5) of Comparative Example 1, using the conjugate release pad produced in step (2) of Comparative Example 1, the sample pad produced in step (4) of Comparative Example 1, and the above-mentioned membrane of the present invention on which anti-DD antibody was immobilized.

Example 2

Verification of the Effect of Preventing Poor Flow Progression of Test Samples Displayed by the Binding Assay Porous Solid Phase According to the Present Invention [1]

(1) Preparation of Model Whole Blood Having a High Ht Value

Whole blood was centrifuged to obtain a blood cell layer. Plasma obtained from the same whole blood was added to the blood cell layer to obtain the model whole blood having a Ht value of 70%.

(2) Test Method

100 μl of the model whole blood was applied to the sample pad of the test strip of the device according to the present invention which was produced in Example 1, and after 15 minutes, whether or not the purplish red line, which originated from the conjugate and indicated the edge of the progressing liquid, reached the absorber located at the end of the test strip was examined with the naked eye. If the purplish red line had reached the absorber located at the end of the test strip, it was judged that the porous solid phase had prevented poor flow progression of the test sample. The results are shown in Table 1. On a related note, in a test in which the conjugate was applied directly onto the membrane of Comparative Example 1, whether the adhesive plastic sheet was present or not did not make any observable difference in the flow progression rate of the test sample.

TABLE 1

| | Name of the surfactant of the present invention | Surfactant classification | Effect |
|---|---|---|---|
| Example 1-1 | n-Octyl-β-D-glucoside | Alkyl glucoside | ○ |
| Example 1-2 | n-Heptyl-β-D-thioglucoside | Alkyl glucoside | ○ |
| Example 1-3 | Sucrose monocaproate | Sucrose fatty acid ester | ○ |
| Comparative Example 1 | no surfactant | no surfactant | X |

(3) Test Results

In the test strip of Comparative Example 1, the purplish red line did not reach the anti-DD antibody line. On the other hand, in the test strips of the present invention comprising n-octyl-β-D-glucoside, n-heptyl-β-D-thioglucoside, or sucrose monocaproate, it was confirmed that the purplish red line had migrated to the absorber located at the end of the test strip.

It was judged from the above that n-octyl-β-D-glucoside, n-heptyl-β-D-thioglucoside, and sucrose monocaproate each had an effect of preventing poor flow progression of the test sample in the porous solid phase for binding assay (marked "○" in the "Effect" column of Table 1).

Example 3

Verification of the Effect of Preventing Poor Flow Progression of Test Samples Displayed by the Binding Assay Porous Solid Phase According to the Present Invention [2]

(1) Preparation of Purified D Dimer (DD)-Containing Model Whole Blood (DD Model Whole Blood) Having a High Ht Value Whole blood was centrifuged to obtain a blood cell layer. A 10 mmol/l Tris-HCl buffer (pH 8.0) containing purified DD and plasma obtained from the same whole blood was added to the blood cell layer, to obtain the model whole blood containing DD at the final concentration of 1.0 μg/ml and having an Ht value of 70% after the reconstitution.

(2) Test Method

100 μl of the DD model whole blood was applied to the sample pad of the immunochromatographic device comprising the binding assay porous solid phase of the present invention (comprising n-octyl-β-D-glucoside) produced in Example 1, and changes in the reflection absorbance (hereafter, in Examples, referred to as "the absorbance") in the detection window of the test device was measured at 1 minute intervals (from 1 minute to 15 minutes after the addition of the sample) by using an immunochromatography reader "ICA-1000" (manufactured by Hamamatsu Photonics K.K.). The same equipment was used for measuring the absorbance in all Examples.

(3) Test Results

Figure 2:
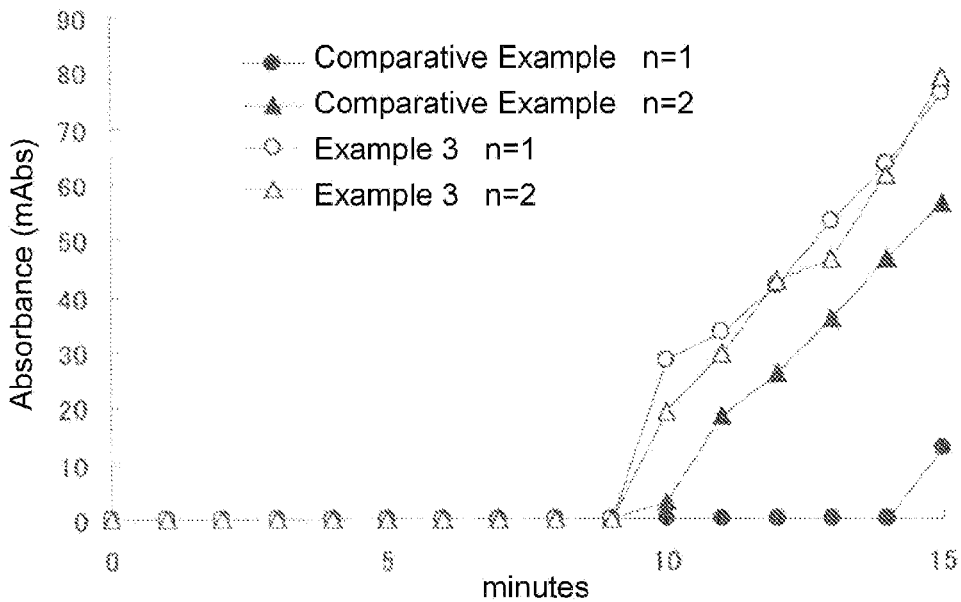
FIG. 2 shows a result of a test in which a model whole blood having a high Ht value was used as a test sample, which verified the present invention's effect of preventing the poor flow progression of the test sample (Example 3).

In the test strip comprising the binding assay porous solid phase of the present invention, an increase in the absorbance was observed 10 minutes after the addition of the DD model whole blood, and the absorbance continued to increase linearly until 15 minutes after the addition of the DD model whole blood. Nearly identical results were obtained in two measurements ("Example" in FIG. 2). In the test strip comprising the binding assay porous solid phase of Comparative Example 1, an increase in the absorbance was not observed until 14 minutes after the addition of the DD model whole blood in the first measurement, and the increase in the absorbance at 15 minutes after the addition of the DD model whole blood was lower than that observed in the test strip of the present invention at 10 minutes after the addition of the DD model whole blood. In the second measurement, an increase in the absorbance was observed at 11 minutes after the addition of the DD model whole blood. However, the absorbance measured at 15 minutes after the addition of the DD model whole blood was lower than that obtained in the test strip of the present invention ("Comparative Example" in FIG. 2).

It was thus confirmed that the test strip of the present invention can perform assays with excellent reproducibility even when whole blood having an extremely low fluid content (e.g. having an Ht value of 70%) is used as a test sample, and that the present invention has a marked effect of preventing poor flow progression of test samples in binding assay porous solid phase.

Example 4

Verification of the Effect of Preventing Poor Flow Progression of Test Samples Displayed by the Binding Assay Porous Solid Phase According to the Present Invention [3]

(1) Preparation of DD Model Whole Blood

DD model whole blood was prepared in the same manner as in Example 3.

(2) Production of an Immunochromatographic Device According to the Present Invention An immunochromatographic device was produced in the same manner as in Example 1 using n-octyl-β-D-glucoside, n-heptyl-β-D-thioglucoside, or sucrose monolaurate as the surfactant.

(3) Test Method

100 μl of the DD model whole blood was applied to the sample pad of the immunochromatographic device of the present invention produced in (2) above, and after 15 minutes, the absorbance in the detection window of the test device was measured (n=5). The CV (%) of the measured values was calculated, and compared with that obtained in an immunochromatographic device comprising a test strip with a conventional binding assay porous solid phase.

(4) Test Results

Figure 3:
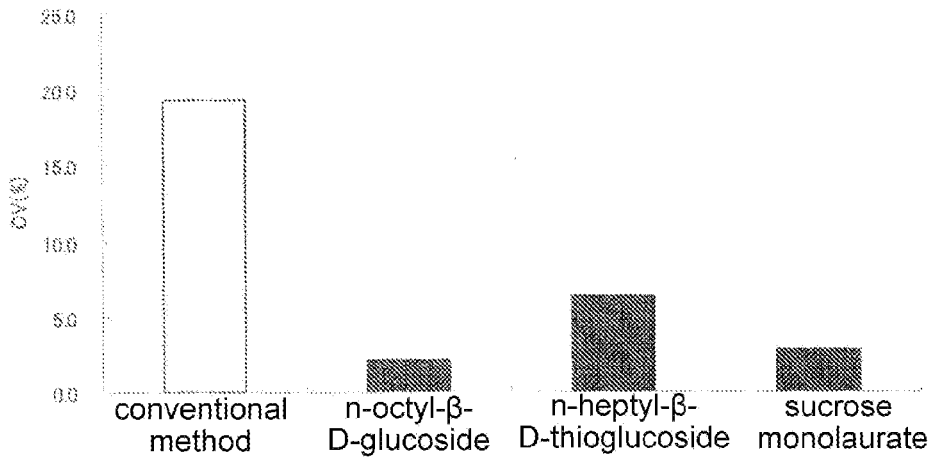
FIG. 3 shows a result of a test in which a model whole blood having a high Ht value was used as a test sample, which verified the present invention's effect of preventing the poor flow progression of the test sample in terms of reproducibility of the measurements (Example 4).

The test strip according to the present invention showed a markedly lower CV (%) as compared with the conventional test strip (see FIG. 3). It was thus confirmed that the use of the binding assay porous solid phase of the present invention enables even those test samples having extremely high Ht values to be assayed with excellent reproducibility, and that the present invention prevents poor flow progression of test samples in binding assay porous solid phase and enables accurate measurements.

Example 5

Verification of the Effect of Preventing Poor Flow Progression of Test Samples Displayed by the Binding Assay Porous Solid Phase According to the Present Invention [4]

(1) Preparation of Purified D Dimer (DD)-Containing Model Whole Blood (DD Model Whole Blood) Having a High Ht Value Whole blood was centrifuged to obtain a blood cell layer. A 10 mmol/l Tris-HCl buffer (pH 8.0) containing a purified DD and plasma obtained from the same whole blood were added to the blood cell layer to obtain model whole blood containing DD at the final concentration of 1.0 μg/ml and having an Ht value of 62%.

(2) Production of a Membrane on which Anti-DD Antibody is Immobilized (Binding Assay Porous Solid Phase)

A membrane on which anti-DD antibody is immobilized (binding assay porous solid phase) was produced in the same manner as in step (1) of Example 1, except that the concentration of the surfactant added to the 10 mmol/l phosphate buffer (pH 7.2) was 0, 0.01, 0.05, 0.075, or 0.10% (w/v).

(3) Test Method

The test method described in step (3) of Example 4 was used. The CV (%) of the measured values was calculated to determine the optimal concentration range.

(4) Test Results

Figure 4:
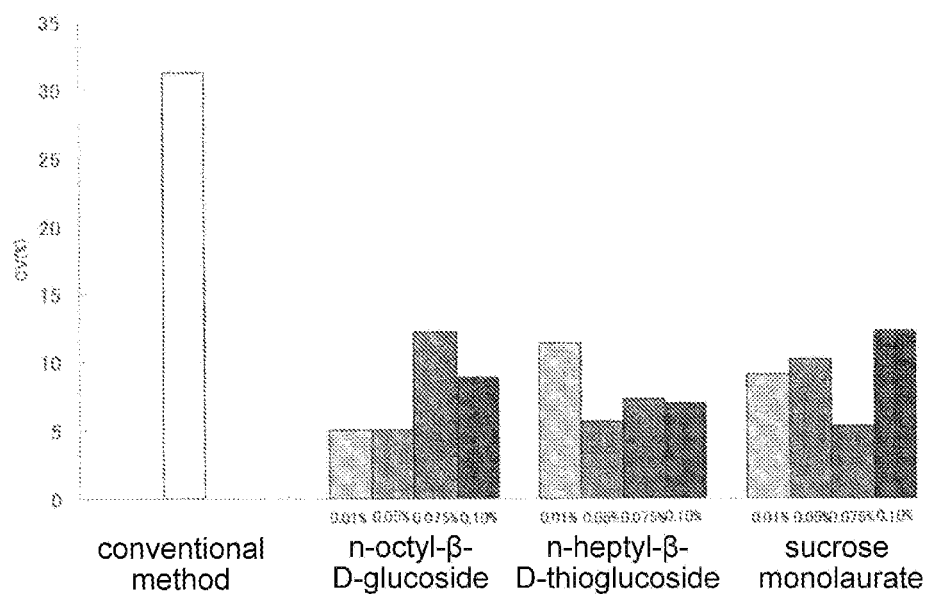
FIG. 4 shows a result of a test in which a model whole blood having a high Ht value was used as a test sample and the concentration of each surfactant was varied, which verified the present invention's effect of preventing the poor flow progression of the test sample in terms of reproducibility of the measurements (Example 5).

As shown in FIG. 4, the use of each surfactant ensured excellent reproducibility at each concentration tested, as compared with the conventional method. When the CV value was equal to or smaller than 15% (i.e. half of that obtained with the conventional method), it was judged that the use of the surfactant was effective. Each surfactant used in the present Example invariably yielded CV values of less than 15% in the concentration range of 0.01 to 0.10%. It was thus confirmed that the use of each of these surfactants provides a satisfactory effect as compared with the conventional method.

Example 6

Production of an Immunochromatographic Device Comprising a Control Line (1) Production of Colloidal Gold-Labeled KLH (KLH Conjugate) for Control Line 10 ml of a 2 mmol/l phosphate buffer (pH 6.1) in which KLH powder had been dissolved (620 μg/ml) was added to 200 ml of a potassium carbonate buffer (pH 8.0) containing colloidal gold at 1 OD/ml (particle diameter: 40 nm). The mixture was stirred at room temperature for 10 minutes. After the addition of 20 ml of 10% bovine serum albumin (BSA) aqueous solution to the colloidal gold-KLH mixture, the mixture was stirred for 5 minutes, and centrifuged (10,000 rpm) at 10° C. for 45 minutes to obtain a sediment (conjugate). The conjugate was diluted with (suspended in) a Conjugate Dilution Buffer (manufactured by Scripps) to 17 OD/ml. The absorbance was measured at 531 nm (i.e., the maximum absorption wavelength of the colloidal gold).

(2) Production of a Conjugate Release Pad

The anti-DD antibody conjugate produced in step (1) of Comparative Example 1 and the KLH conjugate produced in the step (1) above were mixed with a 1.33% casein and 4% sucrose solution (pH 7.5) to prepare a conjugate solution in which the concentrations of the conjugates were 4 OD/ml and 4.5 OD/ml, respectively. A glass fiber pad (width: 13.0 mm, length: 254 mm, thickness: 0.56 mm) ("No. 8964" manufactured by Pall Corporation) was impregnated with 1.2 volumes (relative to the volume of the pad) of the conjugate solution.

The pad was dried at 70° C. for 30 minutes in a dry oven to obtain a conjugate release pad.

(3) Production of a Membrane on which Anti-DD Antibody and Anti-KLH Polyclonal Antibody are Immobilized (Binding Assay Porous Solid Phase)

A nitrocellulose membrane was immersed in a 10 mmol/l phosphate buffer (pH 7.2) containing the surfactant of the present invention at the specified concentration as in step (1) of Example 1, and shaken at room temperature for 30 minutes. After excess liquid was removed, the membrane was dried at 37° C. for 1 hour in a dry oven. 'Lines' of a 10 mmol/l phosphate buffer (pH 7.2) containing 1 mg/ml anti-DD antibody and 2.5% sucrose, and of a 10 mmol/l phosphate buffer (pH 7.2) containing 0.5 mg/ml anti-KLH polyclonal antibody and 2.5% sucrose, were drawn (1 μl/cm) on a nitrocellulose membrane (short side: 25 mm, long side: 254 mm, thickness: 0.235 mm) ("HF240" manufactured by Millipore) along the long side, at the positions which were 11 mm from one end of the long side and 15 mm from the same end, respectively, by using an immunochromatography dispenser "XYZ3050" (manufactured by BIODOT). The membrane was dried at 70° C. for 45 minutes in a dry oven to obtain a membrane on which anti-DD antibody had been immobilized.

(4) Production of a Sample Pad

A sample pad was produced in the same manner as in step (4) of Comparative Example 1.

(5) Production of an Immunochromatographic Device

Figure 5:
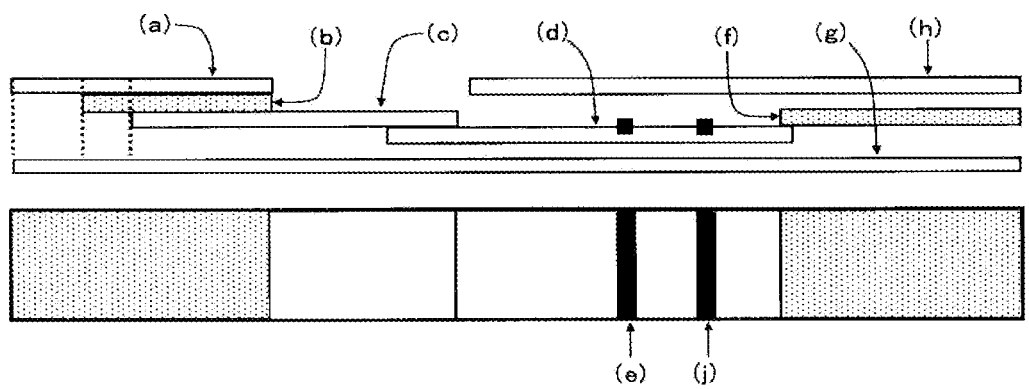
FIG. 5 shows a schematic configuration diagram of a test strip comprising a control line (Example 6).

A test strip comprising a control line, and an immunochromatographic device, were produced in the same manner as in step (5) of Comparative Example 1 using the conjugate release pad produced in (2) above, the membrane produced in (3) above, and the sample pad produced in (4) above. FIG. 5 is a schematic configuration diagram of the test strip.

In Examples 7 and 9 below, the term "test line" refers to a line (which will appear in (e) in FIG. 5) detected when the test sample reaches the position on the membrane (d) where the anti-DD antibody (e) is immobilized, and the term "control line" refers to a line (which will appear in (j) in FIG. 5) detected when the test sample reaches the position on the said membrane where the control capture reagent (anti-KLH polyclonal antibody) is immobilized.

Example 7

Verification of the Effect of Preventing Poor Flow Progression of Test Samples Displayed by the Binding Assay Porous Solid Phase According to the Present Invention [5]

(1) Preparation of Purified D Dimer (DD)-Containing Concentrated Plasma (DD Concentrated Plasma)

Lyophilized plasma (0.5 ml) collected from a healthy person was dissolved in 0.25 ml of purified water to prepare a 2-fold concentrated plasma. A 10 mmol/l Tris HCl buffer (pH 8.0) containing purified DD was added to the concentrated plasma to prepare the DD concentrated plasma having a final DD concentration of 1.0 μg/ml.

(2) Test Method

100 μl of the DD concentrated plasma was applied to the sample pad of the immunochromatographic device produced in Example 6, and after 15 minutes, the absorbance in the detection window of the test device was measured (n=5). The CV (%) of the measured values was calculated, and compared with that obtained with a conventional immunochromatographic device (i.e., the same as the immunochromatographic device of Example 6 except that the surfactant according to the present invention was not included).

(3) Test Results

Figure 6:
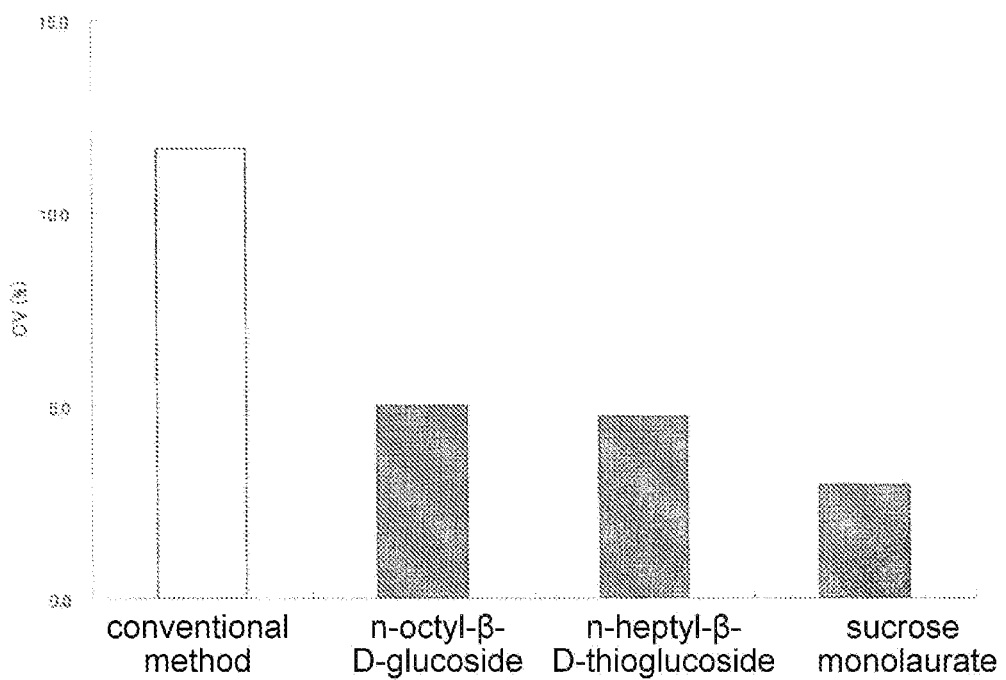
FIG. 6 shows a result of a test in which concentrated plasma was used as a test sample, which verified, in terms of reproducibility of the measurements, the present invention's effect of improving the poor flow progression of the test sample at the test line (Example 7).
Figure 7:
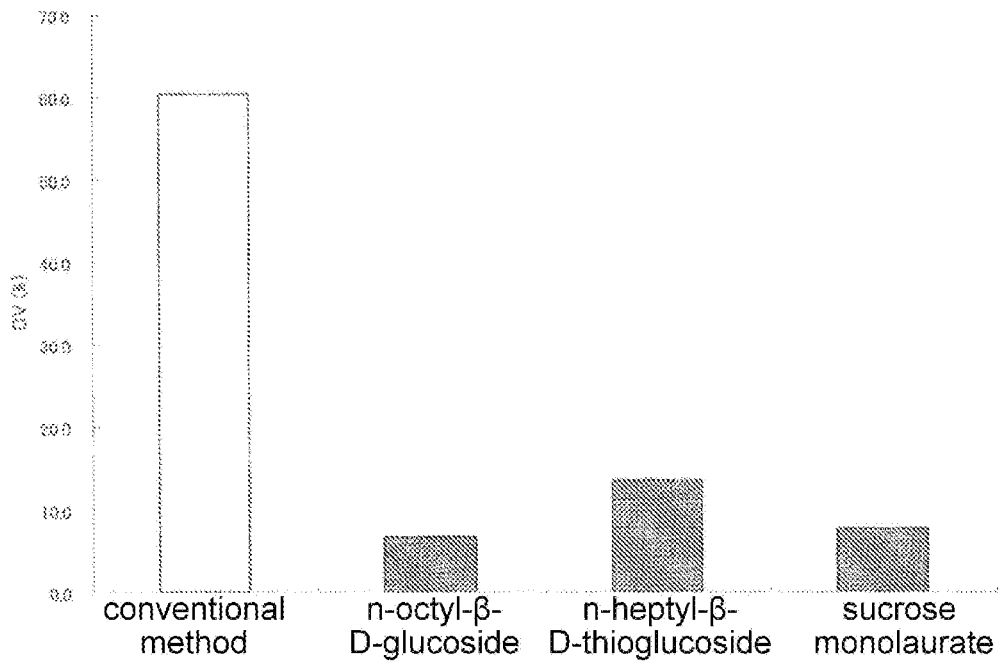
FIG. 7 shows a result of a test in which concentrated plasma was used as a test sample, which verified, in terms of reproducibility of the measurements, the present invention's effect of preventing the poor flow progression of the test sample at the control line (Example 7).

FIG. 6 shows the results of the detection at the test line, and FIG. 7 shows the results of the detection at the control line. The use of each of the surfactants according to the present invention produced lower CV (%) as compared with that measured in the conventional immunochromatographic device. The reproducibility of the detection at the control line was poor in the conventional method because the edge of the progressing test sample did not reach the test line. However, the reproducibility was greatly improved when the binding assay porous solid phase of the present invention was used, due to the prevention of poor flow progression of the test sample. It was thus confirmed that the binding assay porous solid phase of the present invention enables a twofold-concentrated plasma test sample to be assayed with excellent reproducibility, and that the present invention prevents poor flow progression of test samples in binding assay porous solid phase and enables accurate measurements.

Example 8

Verification of the Effect of Preventing Poor Flow Progression of Test Samples Displayed by the Binding Assay Porous Solid Phase According to the Present Invention [6]

(1) Materials and Test Method

The same materials and test method described in Example 2 were used, except that sodium cholate or CHAPS was used as the surfactant.

TABLE 2

|  | Name of the surfactant of the present invention | Surfactant classification | Effect |
| --- | --- | --- | --- |
| Example | Sodium cholate | Steroid | ○ |
| Example | CHAPS | Steroid | ○ |
| Comparative Example | no surfactant | no surfactant | X |

(2) Test Results

The test strip of the present invention comprising sodium cholate allowed the purplish red line to reach the absorber located at the end of the test strip, similarly to the surfactants shown in Example 2.

Therefore it was judged that sodium cholate and CHAPS were effective in preventing poor flow progression of the test sample in the binding assay porous solid phase (marked "○" in the "Effect" column of Table 2).

Example 9

Verification of the Effect of Preventing Poor Flow Progression of Test Samples Displayed by the Binding Assay Porous Solid Phase According to the Present Invention [7]

(1) Materials and Test Method

The same materials and test method described in Example 4 were used, except that sodium cholate or CHAPS was used as the surfactant.

(2) Test Results

Figure 8:
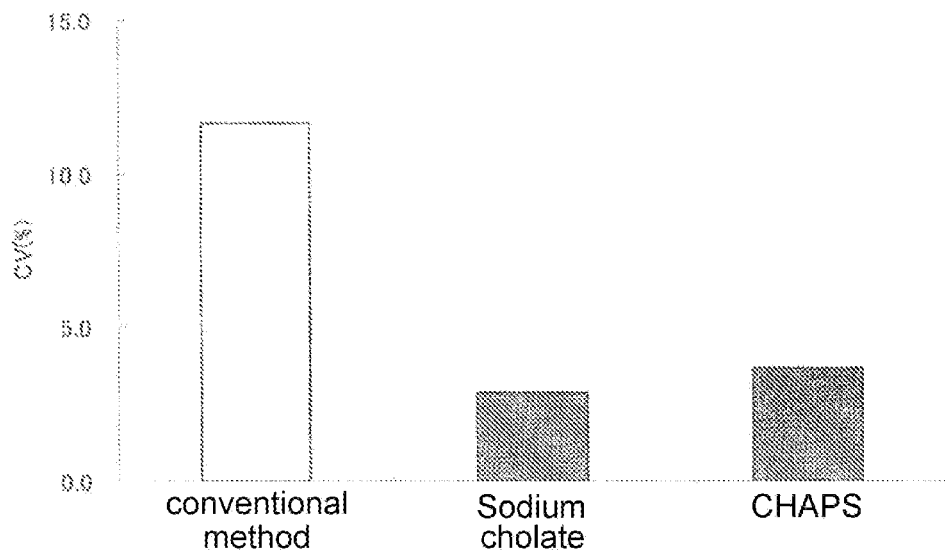
FIG. 8 shows a result of a test in which concentrated plasma was used as a test sample, which verified, in terms of reproducibility of the measurements, the present invention's effect of preventing the poor flow progression of the test sample at the test line (Example 9).
Figure 9:
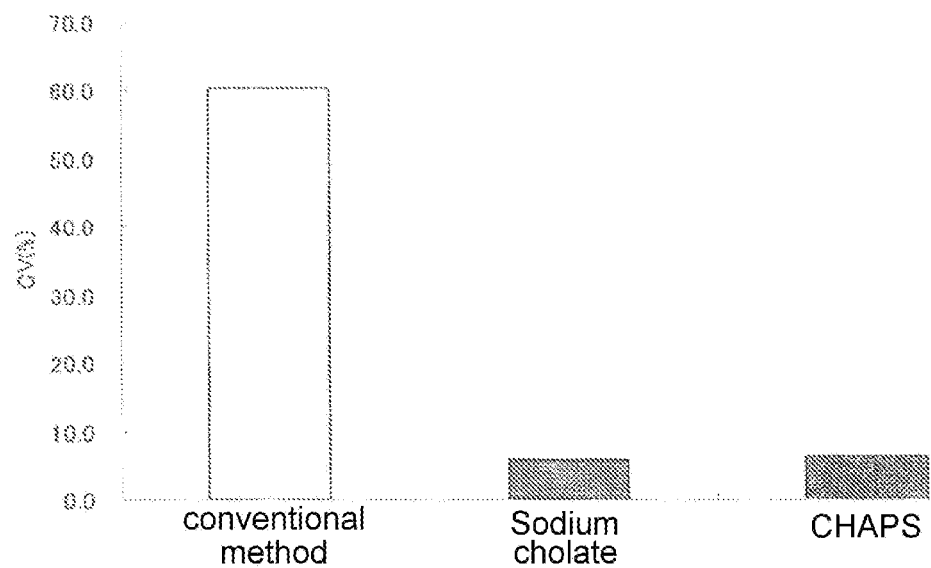
FIG. 9 shows a result of a test in which concentrated plasma was used as a test sample, which verified, in terms of reproducibility of the measurements, the present invention's effect of preventing the poor flow progression of the test sample at the control line (Example 9).

FIG. 8 shows the results of the detection at the test line, and FIG. 9 shows the results of the detection at the control line. The test strip according to the present invention treated with sodium cholate or CHAPS showed a markedly lower CV (%) at the test line as well as the control line, compared to the conventional test strip (see FIGS. 8 and 9). The CV (%) in the conventional method was quite high for the detection at the control line. This was because the test sample did not reach the control line due to poor flow progression. It was thus confirmed that a test sample having a high Ht value can be assayed with excellent reproducibility also with the use of sodium cholate or CHAPS.

Example 10

Use of Two Types of Colloidal Gold Differing in Particle Diameter (1) Addition of 60 nm Colloidal Gold-Labeled Anti-D Dimer Antibody 10 ml of a 2 mmol/l borate buffer (pH 8.0) containing 46.2 µg/ml of an anti-D dimer monoclonal antibody (anti-DD antibody) was added to 200 ml of a potassium carbonate buffer (pH 8.0) containing colloidal gold (particle diameter: 60 nm) at 1 OD/ml. The mixture was stirred at room temperature for 10 minutes. After the addition of 10 ml of a 10% bovine serum albumin (BSA) aqueous solution, the colloidal gold-anti-DD antibody mixture was stirred for 5 minutes, and centrifuged (10,000 rpm) at 10° C. for 45 minutes to obtain a sediment (conjugate). The conjugate was diluted with (suspended in) a Conjugate Dilution Buffer (manufactured by Scripps) to 17 OD/ml. The absorbance was measured at 531 nm (i.e., the maximum absorption wavelength of the colloidal gold).

(2) Production of a Conjugate Release Pad

A 40 nm colloidal gold-labeled anti-DD antibody and a 60 nm colloidal gold-labeled DD antibody were mixed with a 1.33% casein and 4% sucrose solution (pH 7.5) to prepare a conjugate solution in which each antibody was adjusted to 4 OD/ml. A glass fiber pad (width: 13.0 mm, length: 254 mm, thickness: 0.56 mm) ("No. 8964" manufactured by Pall Corporation) was impregnated with 1.2 volumes (relative to the volume of the pad) of the conjugate solution. The pad was dried at 70° C. for 30 minutes in a dry oven to obtain a conjugate release pad.

(3) Production of an Immunochromatographic Device According to the Present Invention An immunochromatographic device was produced in the same manner as in Example 1, except that the conjugate release pad produced in (2) above was used. n-Heptyl-β-D-thioglucoside was used as the surfactant.

(3) Preparation of Purified D Dimer (DD)-Containing Model Whole Blood (DD Model Whole Blood) Having a High Ht Value Whole blood was centrifuged to obtain a blood cell layer. A 10 mmol/l Tris-HCl buffer (pH 8.0) containing purified DD and plasma obtained from the same whole blood were added to the blood cell layer, to obtain DD model whole blood having an Ht value of 60%. The DD concentration was adjusted to 0, 3.0, or 15 µg/ml.

(4) Test Results

Figure 10:
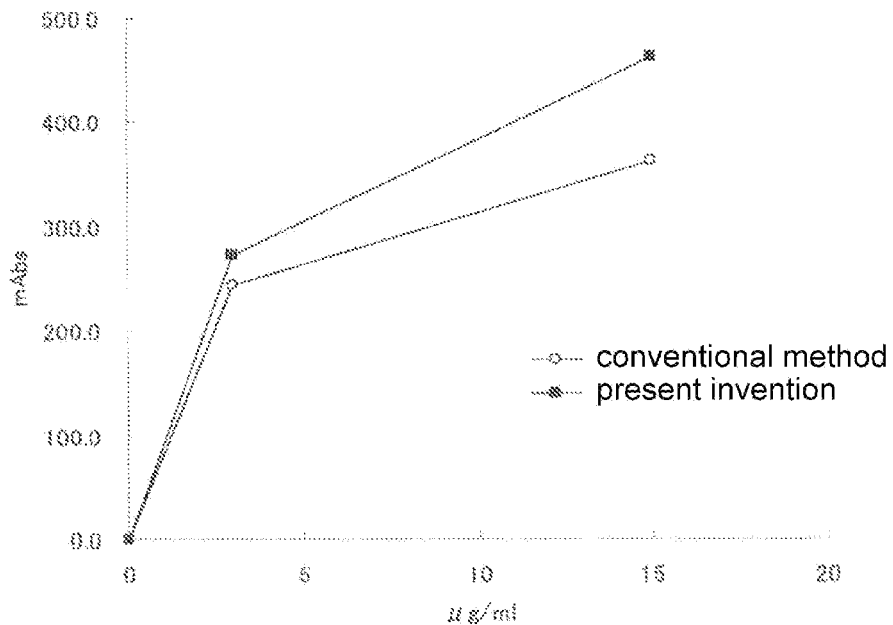
FIG. 10 shows a result of a test in which two types of colloidal gold differing in particle diameter were used with the porous solid phase of the present invention, which verified the present invention's effect of preventing the poor flow progression of the test sample (Example 10).

In the assay system in which two types of colloidal gold differing in particle diameter were used, the use of the porous solid phase of the present invention improved the detection sensitivity as compared with the conventional method (in which colloidal gold of single particle diameter was used), and enabled the test sample containing the analyte at a high concentration to be analyzed in a more quantitative fashion (FIG. 10).

Example 11

Verification of the Effect of Preventing Poor Flow Progression of Test Samples Displayed by the Binding Assay Porous Solid Phase According to the Present Invention [8]

(1) Preparation of Purified D Dimer (DD)-Containing Model Whole Blood (DD Model Whole Blood) Having High Ht Value Whole blood was centrifuged to obtain a blood cell layer. A 10 mmol/l Tris-HCl buffer (pH 8.0) containing purified DD and plasma obtained from the same whole blood were added to the blood cell layer to obtain model whole blood containing DD at the final concentration of 1.0 µg/ml and having an Ht value of 60%.

(2) Production of a Membrane on which Anti-DD Antibody is Immobilized (Binding Assay Porous Solid Phase)

A membrane on which anti-DD antibody was immobilized (binding assay porous solid phase) was produced in the same manner as in step (1) of Example 1, except that sodium cholate was used as the surfactant and the concentration of the surfactant added to the 10 mmol/l phosphate buffer (pH 7.2) was 0, 0.01, 0.05, 0.075, 0.1, or 0.5% (w/v).

(3) Test Method

The test method described in step (3) of Example 4 was used. The CV (%) of the measured values was calculated to determine the optimal concentration range.

(4) Test Results

Figure 11:
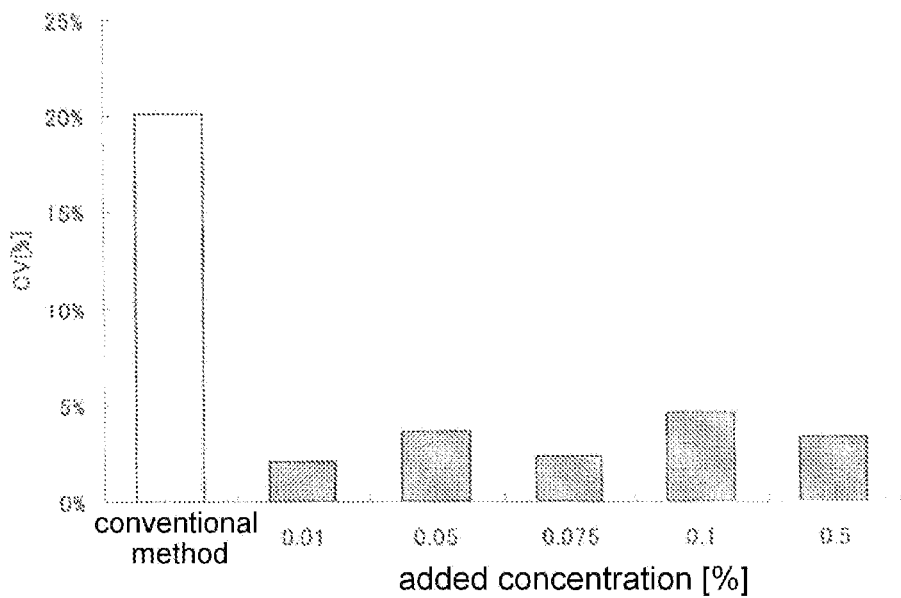
FIG. 11 shows a result of a test in which a model whole blood having a high Ht value was used as a test sample and the concentration of sodium cholate was varied, which verified the present invention's effect of preventing the poor flow progression of the test sample in terms of assay reproducibility (Example 11)

As shown in FIG. 11, the use of the surfactant at each concentration tested provided excellent reproducibility as compared with the conventional method. When the CV value was equal to or smaller than 10% (i.e. half of that obtained in the conventional method), it was judged that the use of the surfactant was effective. The surfactant used in the present Example invariably yielded CV values of less than 10% in the concentration range of 0.01 to 0.5%. It was thus confirmed that the use of the surfactant provides a satisfactory effect as compared with the conventional method.

Example 12

Comparison of the Effects of Preventing Disturbance in the Measurement Waveforms Obtained with the Pretreatments of the Binding Assay Porous Solid Phases with the Surfactant of the Present Invention and with Other Surfactants (1) Preparation of Purified D Dimer (DD)-Containing Concentrated Plasma (DD Concentrated Plasma)

Lyophilized plasma (0.5 ml) collected from a healthy person was dissolved in 0.25 ml of purified water to prepare a 2-fold concentrated plasma. A 10 mmol/l Tris HCl buffer (pH 8.0) containing purified DD was added to the said concentrated plasma to prepare DD concentrated plasma having a final DD concentration of 1.0 μg/ml.

(2) Production of an Immunochromatographic Device

A membrane on which anti-DD antibody and anti-KLH polyclonal antibody were immobilized was produced in the same manner as in step (3) of Example 6, except that 0.05% n-heptyl-β-D-thioglucoside, 0.05% Tween 20, or 0.05% Triton X-100 was used as the surfactant in the 10 mmol/l phosphate buffer (pH 7.2). An immunochromatographic device was produced in the same manner as in step (5) of Example 6 using the said membrane.

(3) Test Method

120 μl of the DD concentrated plasma was applied to the sample pad of the immunochromatographic device produced in (2) above, and after 15 minutes, the absorbance in the detection window of the test device was measured (n=5). The shape of the measurement waveform was examined in each measurement.

The immunochromatographic device of the present invention (n-heptyl-β-D-thioglucoside pretreatment) was compared with the immunochromatographic device comprising a nitrocellulose membrane that was not impregnated with surfactant (conventional method), and the immunochromatographic device in which the surfactant used for impregnating the solid phase was Triton X-100 or Tween 20 (Triton X-100 pretreatment or Tween 20 pretreatment).

(4) Test Results

Figure 12:
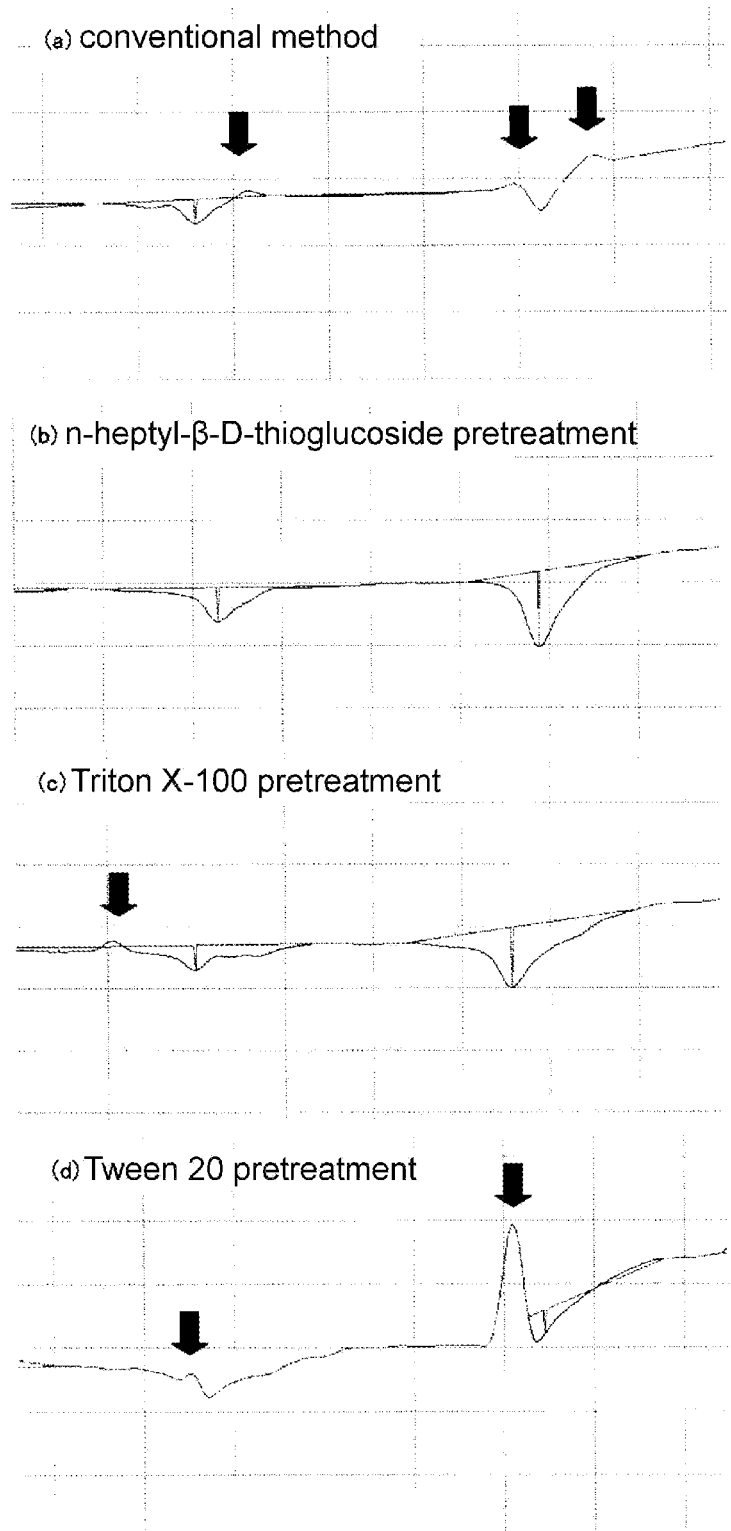
FIG. 12 shows a result of a test in which concentrated plasma was used as a test sample and the porous solid phase was pretreated either with a surfactant of the present invention or other surfactants, which verified whether the effect of preventing the disturbance in the measurement waveform was present with each surfactant (Example 12).

FIG. 12 shows the shapes of the measurement waveforms under the different experimental conditions. To the left of the figure is the upstream side, to the right is the downstream side, and a downward peak represents a signal. The peak appearing first corresponds to the test line, and the peak appearing subsequently corresponds to the control line. Since the reflection absorbance is calculated from the ratio between the reflected light intensities at the peak and around the peak, a change in the reflected light intensity around the peak affects the accuracy of the measurement. Therefore, it would be ideal if the reflected light intensity around the peak is unchanged.

As shown in FIG. 12, an upward change in the reflected light intensity was observed around the peaks in the waveforms in (a) conventional method, (c) Triton X-100 pretreatment and (d) Tween 20 pretreatment. In particular, a drastic change in the reflected light intensity was observed in the porous solid phase pretreated with Tween 20 ((d) in FIG. 12).

In the porous solid phase pretreated with the surfactant according to the present invention, however, a change in the reflected light intensity around the peaks was not observed ((b) in FIG. 12).

Figure 13:
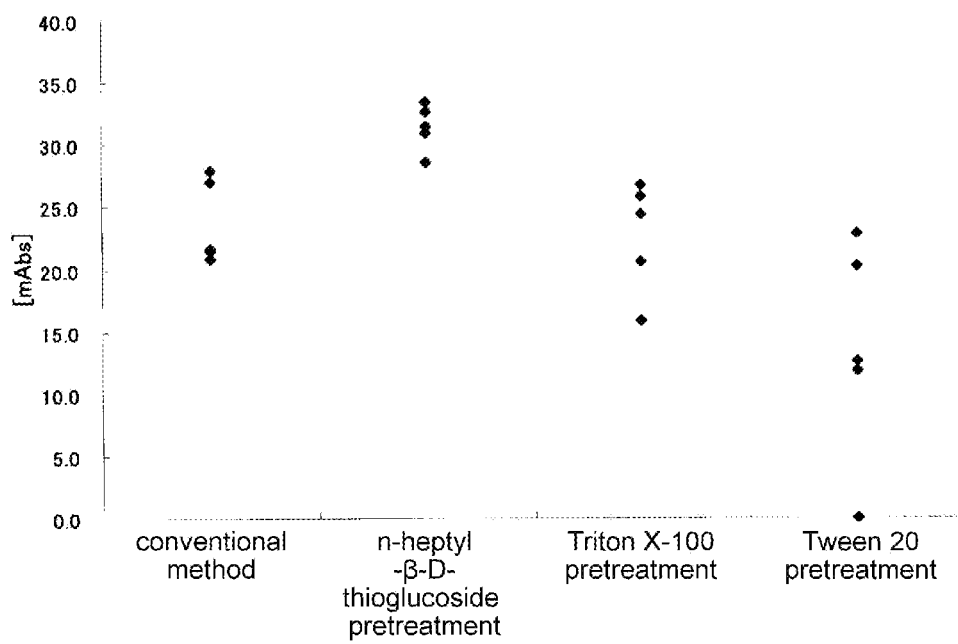
FIG. 13 shows a result of a test in which concentrated plasma was used as a test sample and the porous solid phase was pretreated either with a surfactant of the present invention or other surfactants, which verified whether an improved sensitivity/reproducibility could be improved (Example 12).

FIG. 13 shows the distribution of reflection absorbance at the test line. When the porous solid phase pretreated with the surfactant according to the present invention was used, the variance of the measured reflection absorbance values was small (i.e. reproducibility was excellent), and the sensitivity was high. On the other hand, the variance of the measured values was large in other conditions. In particular, when Tween 20 was used, the reflection absorbance could not be even calculated (i.e. measurement was impossible) sometimes.

Example 13

Comparison of the Effects of Preventing Disturbance in Measurement Waveforms Among Different Methods of Incorporating Surfactant to Porous Solid Phase (1) Preparation of Purified D Dimer (DD)-Containing Concentrated Plasma (DD Concentrated Plasma)

DD concentrated plasma was prepared in the same manner as in Example 12.

(2) Preparation of Solid Phase Washing Solutions n-Heptyl-β-D-thioglucoside, Tween 20, or Triton X-100 was added to a 10 mmol/l phosphate buffer (pH 7.2) (final concentration: 0.05% (w/v)) to prepare a solid phase washing solution.

(3) Test Method

120 μl of the DD concentrated plasma was applied to the sample pad of the test strip according to the present invention or the test strip produced by the conventional method. The absorbance in the detection window of the test device of the present invention was measured 15 minutes after the addition of the DD concentrated plasma. For the test device of the conventional method, 50 μl of the solid phase washing solution was added 5 minutes after the addition of the DD concentrated plasma, and the absorbance in the detection window was measured 15 minutes after the addition of the DD concentrated plasma.

(4) Test Results

Figure 14:
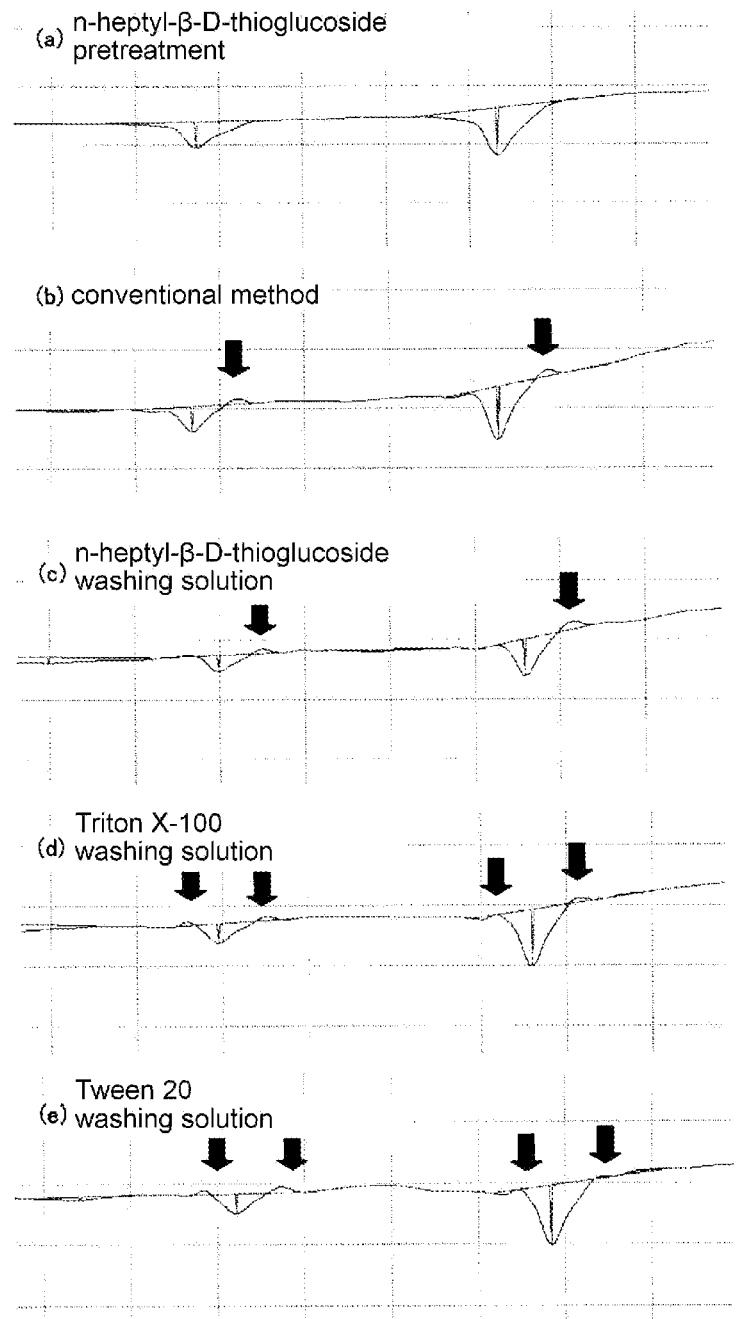
FIG. 14 shows a result of a test in which concentrated plasma was used as a test sample and a surfactant of the present invention and other surfactants were used in a different way than the present invention's method to test whether the disturbance in the measurement waveforms could be prevented (Example 13).

When the surfactant of the present invention was added to the porous solid phase in the form of the solid phase washing solution, the disturbance of measurement waveform was not prevented (arrows in FIG. 14 (c)). Likewise, the disturbance of measurement waveform was not prevented when (b) the conventional method, (d) the solid phase washing solution containing Triton X-100, or (e) the solid phase washing solution containing Tween 20 was used (FIG. 14).

In contrast, when the porous solid phase was pretreated with the surfactant according to the present invention, a change in reflected light intensity around the peaks was not observed (FIG. 14 (a)).

Figure 15:
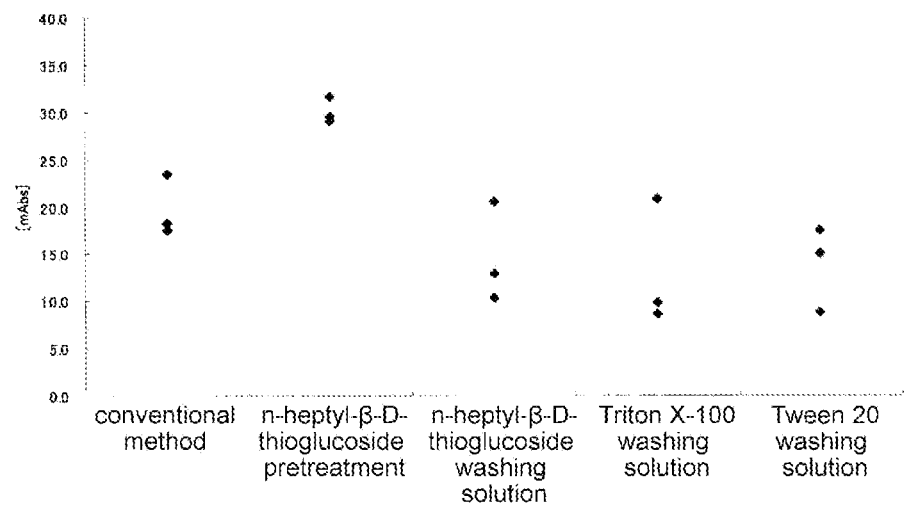
FIG. 15 shows a result of a test in which concentrated plasma was used as a test sample and a surfactant of the present invention and other surfactants were used in a different way than the present invention's method to test whether sensitivity/reproducibility could be improved (Example 13).

FIG. 15 shows the distribution of the reflection absorbance at the test line. When the porous solid phase pretreated with the surfactant according to the present invention was used, the variance of the measured reflection absorbance values was small (i.e. reproducibility was excellent) and the sensitivity was high. On the other hand, variance of the measured values was large under other conditions.

It was thus confirmed that the porous solid phase according to the present invention may prevent not only the poor flow progression of test samples but also the disturbance in the measurement waveforms, and that it is capable of performing assays with higher sensitivity and greater reproducibly as compared with the conventional method or the use of a solid phase washing solution (FIG. 15).

Example 14

Verification of the Effect of Improving the Reproducibility Associated with an Addition of Anticoagulant to the Sample Pad (1) Preparation of Purified D Dimer (DD)-Containing Whole Blood (DD Whole Blood)

A 10 mmol/l Tris HCl buffer (pH 8.0) containing purified DD was added to whole blood collected from a healthy person to prepare DD whole blood having a final DD concentration of 1.0 μg/ml.

(2) Production of an Immunochromatographic Device Using a Sample Pad Containing an Anticoagulant An immunochromatographic device was produced in the same manner as in Comparative Example 1, except that the sample pad was impregnated with the sample pad impregnation solution to which an anticoagulant was added. The types and the final concentrations of the anticoagulants were as follows.
EDTA-2Na (EDTA: 1 or 5 mmol/l)
Diethylenetriamine-N,N,N',N'',N''-pentaacetic acid (DTPA: 1 mmol/l)
trans-1,2-Diaminocyclohexane-N,N,N',N'-tetraacetic acid (CyDTA: 1 mmol/l)

(3) Test Method

120 μl of the DD whole blood was applied to the sample pad of the immunochromatographic device which had been treated with the anticoagulant, and after 15 minutes, the absorbance in the detection window of the test device was measured.

(4) Test Results

Figure 16:
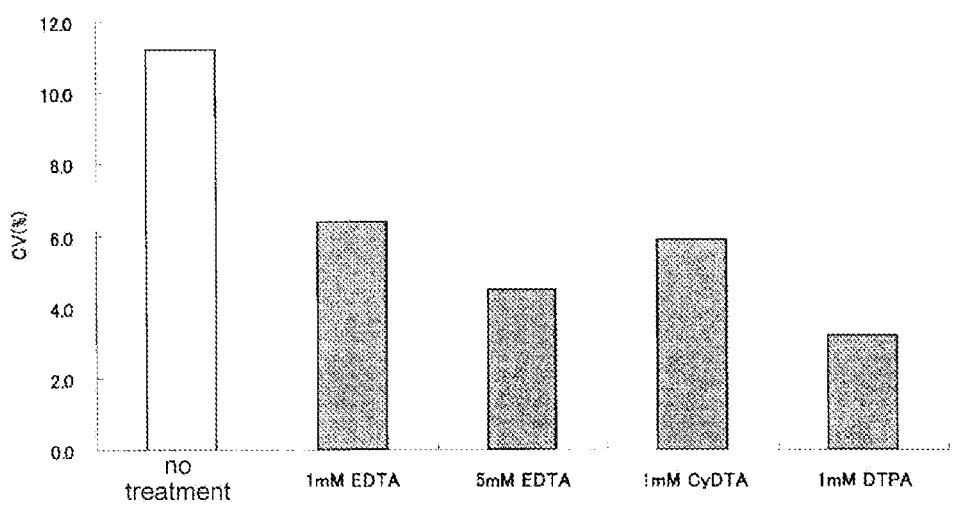
FIG. 16 shows a result of a test in which whole blood collected from a healthy person was used as a test sample and various anticoagulants were added to the sample pad to verify the effect of preventing the poor flow progression of the test sample in terms of measurement reproducibility (Example 14).

When the test strips comprising the sample pads treated with the anticoagulants were used, the reproducibility was improved, regardless of the types of anticoagulants, as compared with the test strip comprising the sample pad not treated with anticoagulant (FIG. 16).

Example 15

Verification of the Effect of Improving the Reproducibility Associated with an Addition of Amino Acid to the Conjugate Release Pad (1) Preparation of Purified D Dimer (DD)-Containing Plasma (DD Plasma)

A 10 mmol/l Tris HCl buffer (pH 8.0) containing purified DD was added to plasma collected from a healthy person to prepare DD plasma having a final DD concentration of 1.0 μg/ml.

(2) Addition of Amino Acid to the Conjugate Release Pad

An immunochromatographic device was produced in the same manner as in Comparative Example, except that the conjugate release pad was produced with the conjugate solution to which an amino acid had been added. The amino acid added was serine, glycine, glutamine, arginine, or alanine. The final concentration of the amino acid was 10 mmol/l in each case.

(3) Test Method

120 μl of the DD plasma was applied to the sample pad of the immunochromatographic device having the conjugate release pad containing the amino acid, and after 15 minutes, the absorbance in the detection window of the test device was measured.

(4) Test Results

Figure 17:
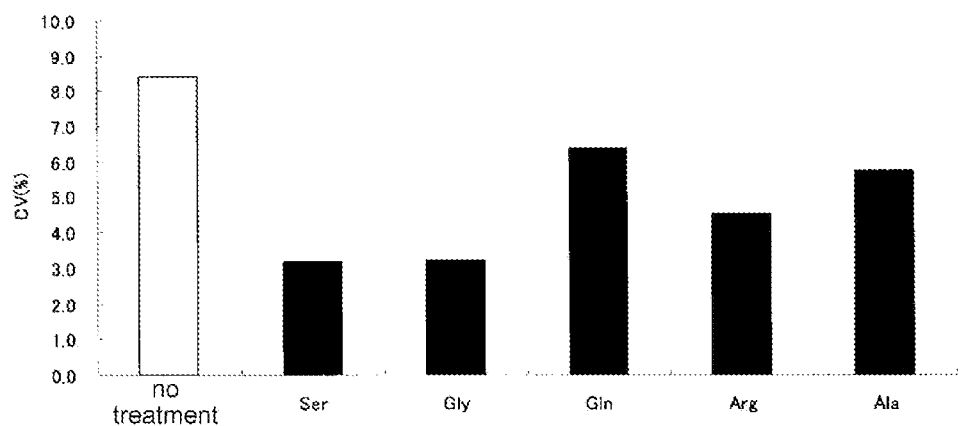
FIG. 17 shows a result of a test in which plasma collected from a healthy person was used as a test sample and various amino acids were added to the conjugate release pad to verify the effect of preventing the poor flow progression of the test sample in terms of measurement reproducibility (Example 15).

The reproducibility was improved when an amino acid was added to the conjugate release pad. In particular, the reproducibility was improved considerably when serine or glycine was added (FIG. 17).

To summarize the results of the Examples, it is concluded from the test results that the use of the binding assay porous solid phase treated with the surfactant according to the present invention allows even highly viscous test samples to flow/progress properly in the porous solid phase, suppresses the disturbance in measurement waveforms, and enables assays with high sensitivity and excellent reproducibility. The reproducibility can be further improved by combining the binding assay porous solid phase of the present invention with a sample pad treated with an anticoagulant and/or a conjugate release pad treated with an amino acid.

INDUSTRIAL APPLICABILITY

According to the present invention, it has become possible to allow even a highly viscous test sample to flow/progress properly in a porous solid phase, and perform assays thereof with excellent reproducibility while preventing false negatives and false positives, by using one or more surfactants selected from (A)-(C) below in the binding assay porous solid phase in which the test sample is allowed to flow/progress: (A) a sugar-containing surfactant that comprises a compound shown by the general formula (I), (B) a sugar-containing surfactant that comprises a sucrose fatty acid ester wherein the constituent fatty acid has 5 to 14 carbon atoms, and (C) a steroid surfactant.

KEYS TO SYMBOLS (a) Sample pad
(b) Conjugate release pad (c) Blood cell separation pad
(d) Porous solid phase (membrane)
(e) Capture reagent (antibody)
(f) Absorber
(g) Adhesive plastic sheet
(h) Polyester film
(j) Control capture reagent

The invention claimed is:

1. A porous solid phase for a binding assay in which at least one surfactant and at least one capture reagent has been incorporated prior to addition of a test sample, the at least one surfactant being selected from the group consisting of:
  n-octyl-β-D-glucoside (n-octyl-β-D-glucopyranoside), n-nonyl-β-D-maltopyranoside, n-heptyl-β-D-thioglucoside (n-heptyl-β-D-thioglucopyranoside), n-nonyl-β-D-thiomaltopyranoside, octyl-β-D-thiogalactopyranoside, dehydrocholates, and 3-[(3-cholamidopropyl)dimethylammonio]propanesulfonic acid,
  wherein the porous solid phase is obtained by the method consisting of the steps of: immersing and shaking a porous membrane in a solution consisting of said at least one surfactant or a solution consisting of a buffer and said at least one surfactant; removing excess of the solution and drying the porous membrane; and then drawing a line or lines of said at least one capture reagent on the porous membrane and drying the membrane, and
  wherein the surfactant and capture reagent are immobilized onto the porous solid phase and present in a dry state, wherein the porous solid phase is suitable for use in a binding assay that is an immunoassay comprising:
  (a) applying the test sample to a binding assay strip that comprises a sample pad, a conjugate release pad comprising an antibody labeled with a visualizable microparticle as a detection reagent, a blood cell separation pad, and the porous solid phase comprising the at least one surfactant on which a capture reagent is immobilized to obtain a specific complex when the test sample passes through the conjugate release pad by reacting the labeled antibody with the test sample; and
  (b) detecting the signal derived from the specific complex that has been captured by the capture reagent.

2. The porous solid phase for a binding assay according to claim 1, wherein the binding assay is a lateral-flow format, dipstick format, or flow-through format assay.

3. The porous solid phase for a binding assay according to claim 1, wherein the capture reagent is an antibody, a specific capture substance, or an antigen.

4. A binding assay strip comprising the porous solid phase for binding assay according to claim 1.

5. The binding assay strip according to claim 4, further comprising a conjugate release pad that contains a detection reagent.

6. The binding assay strip according to claim 5, wherein the detection reagent is a labeled antibody, a labeled specific capture substance, or a labeled antigen.

7. The binding assay strip according to claim 6, wherein the label comprises two types of colloidal gold that differ in particle diameter.

8. The binding assay strip according to claim 5, wherein the conjugate release pad contains an amino acid.

9. The binding assay strip according to claim 3, further comprising a sample pad and/or a blood cell separation pad.

10. The binding assay strip according to claim 9, wherein the sample pad contains an anticoagulant.

11. A binding assay strip for a lateral-flow format binding assay, comprising: (1) a sample pad;
  (2) a conjugate release pad that contains a detection reagent and is placed beneath the sample pad in contact with the sample pad;
  (3) a blood cell separation pad that is placed between the conjugate release pad and a porous solid phase; and
  (4) the porous solid phase, on which a capture reagent is immobilized,
  wherein the porous solid phase is the porous solid phase for binding assay according to claim 1.

12. A device comprising the binding assay strip according to claim 4.

13. The porous solid phase for a binding assay according to claim 1, wherein the binding assay is a lateral-flow format or a dipstick format assay and the porous solid phase comprises a test sample migration area, wherein the surfactant is immobilized to at least the test sample migration area.

* * * * *

UNITED STATES PATENT AND TRADEMARK OFFICE
CERTIFICATE OF CORRECTION

| | | |
|---|---|---|
| PATENT NO. | : 9,110,058 B2 | Page 1 of 2 |
| APPLICATION NO. | : 13/000110 | |
| DATED | : August 18, 2015 | |
| INVENTOR(S) | : Miwako Yoshimizu et al. | |

It is certified that error appears in the above-identified patent and that said Letters Patent is hereby corrected as shown below:

IN THE CLAIMS:

At column 31, lines 9-42 amend claim 1 to read as follows:

-- 1. A porous solid phase for a binding assay in which at least one surfactant and at least one capture reagent has been incorporated prior to addition of a test sample, the at least one surfactant being selected from the group consisting of:

n-octyl-β-D-glucoside (n-octyl-β-D-glucopyranoside) and n-heptyl-β-D-thioglucoside (n-heptyl-β-D-thioglucopyranoside), wherein the porous solid phase is obtained by the method consisting of the steps of: immersing and shaking a porous membrane in a solution consisting of said at least one surfactant or a solution consisting of a buffer and said at least one surfactant; removing excess of the solution and drying the porous membrane; and then drawing a line or lines of said at least one capture reagent on the porous membrane and drying the membrane, and wherein the surfactant and capture reagent are immobilized onto the porous solid phase and present in a dry state, wherein the porous solid phase is suitable for use in a binding assay that is an immunoassay comprising:

(a) applying the test sample to a binding assay strip that comprises a sample pad, a conjugate release pad comprising an antibody labeled with a visualizable microparticle as a detection reagent, a blood cell separation pad, and the porous solid phase comprising the at least one surfactant on which a capture reagent is immobilized to obtain a specific complex when the test sample passes through the conjugate release pad by reacting the labeled antibody with the test sample; and (b) detecting the signal derived from the specific complex that has been captured by the capture reagent. --

At column 32, lines 23-33 amend claim 11 to read as follows:

-- A binding assay strip for a lateral-flow format binding assay, comprising:
(1) a sample pad;
(2) a conjugate release pad that contains a detection reagent and is placed beneath the sample pad in contact with the sample pad;

Signed and Sealed this
First Day of March, 2016

Michelle K. Lee
*Director of the United States Patent and Trademark Office*

(3) a blood cell separation pad that is placed between the conjugate release pad and a porous solid phase; and (4) the porous solid phase, on which a capture reagent is immobilized, wherein the porous solid phase is the porous solid phase for binding assay according to claim 1. --